(12) United States Patent
Holtwick et al.

(10) Patent No.: US 9,884,156 B2
(45) Date of Patent: Feb. 6, 2018

(54) LOCKOUT ELEMENT FOR DISPENSE INTERFACE

(75) Inventors: Marc Holtwick, Frankfurt am Main (DE); Ilona Eggert, Frankfurt am Main (DE); James Alexander Davies, Warwickshire (GB); Simon Lewis Bilton, Warwickshire (GB); David Moore, Leicestershire (GB); Steven Wimpenny, Warwickshire (GB); Christopher Nigel Langley, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 14/113,396

(22) PCT Filed: Apr. 26, 2012

(86) PCT No.: PCT/EP2012/057692
§ 371 (c)(1),
(2), (4) Date: Oct. 23, 2013

(87) PCT Pub. No.: WO2012/146677
PCT Pub. Date: Nov. 1, 2012

(65) Prior Publication Data
US 2014/0039390 A1    Feb. 6, 2014

Related U.S. Application Data

(60) Provisional application No. 61/480,063, filed on Apr. 28, 2011.

(30) Foreign Application Priority Data

Jul. 8, 2011  (EP) ..................... 11173278

(51) Int. Cl.
*A61M 5/50* (2006.01)
*A61M 5/19* (2006.01)
(Continued)

(52) U.S. Cl.
CPC ................ *A61M 5/50* (2013.01); *A61M 5/19* (2013.01); *A61M 5/34* (2013.01); *A61M 5/31535* (2013.01); *A61M 5/31538* (2013.01)

(58) Field of Classification Search
CPC .......... A61M 5/31535; A61M 5/31536; A61M 5/31538; A61M 2005/3154;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| EP | 0937471 | 8/1999 |
| EP | 0937476 | 8/1999 |

(Continued)

OTHER PUBLICATIONS

International Search Report for Int. App. No. PCT/EP2012/057692, completed Aug. 13, 2012.

*Primary Examiner* — Bhisma Mehta
*Assistant Examiner* — William Frehe
(74) *Attorney, Agent, or Firm* — McDonnell Boehnen Hulbert & Berghoff LLP

(57) ABSTRACT

The invention is related to an apparatus comprising a dispense interface for use with a drug delivery device, the dispense interface comprising a lockout element being arranged at least partially between an outer body of the dispense interface and an inner body of the dispense interface and wherein the lockout element is configured to be (Continued)

removeably maintained in a first position, such that when the dispense interface is first attached and then removed from said drug delivery device, the lockout element moves into a second position, wherein the lockout element in the second position is configured to prevent said dispense interface from being reattached to a drug delivery device.

13 Claims, 26 Drawing Sheets

(51) Int. Cl.
*A61M 5/34* (2006.01)
*A61M 5/315* (2006.01)

(58) Field of Classification Search
CPC .... A61M 5/31541; A61M 5/50; A61M 5/504; A61M 39/16; A61M 2039/1022
USPC .................................................. 604/110, 111
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,391,003 B1 * | 5/2002 | Lesch, Jr. ..................... 604/110 | |
| 6,749,588 B1 * | 6/2004 | Howell ............... A61M 5/3273 604/110 |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2003/0060776 A1 | 3/2003 | Heiniger | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0038187 A1 * | 2/2007 | Albert ................. A61M 5/3273 604/164.08 |
| 2008/0154192 A1 * | 6/2008 | Schraga ........................ 604/110 | |
| 2008/0177238 A1 | 7/2008 | Follman et al. | |
| 2009/0275916 A1 | 11/2009 | Harms et al. | |
| 2010/0114035 A1 | 5/2010 | Schubert et al. | |

FOREIGN PATENT DOCUMENTS

| | | |
|---|---|---|
| JP | 2003-525087 | 8/2003 |
| JP | 2008-212645 | 9/2008 |
| JP | 2010-519989 | 6/2010 |
| WO | 99/38554 | 8/1999 |
| WO | 01/10484 | 2/2001 |
| WO | WO 2010147552 A1 * | 12/2010 ............ A61M 5/326 |

\* cited by examiner

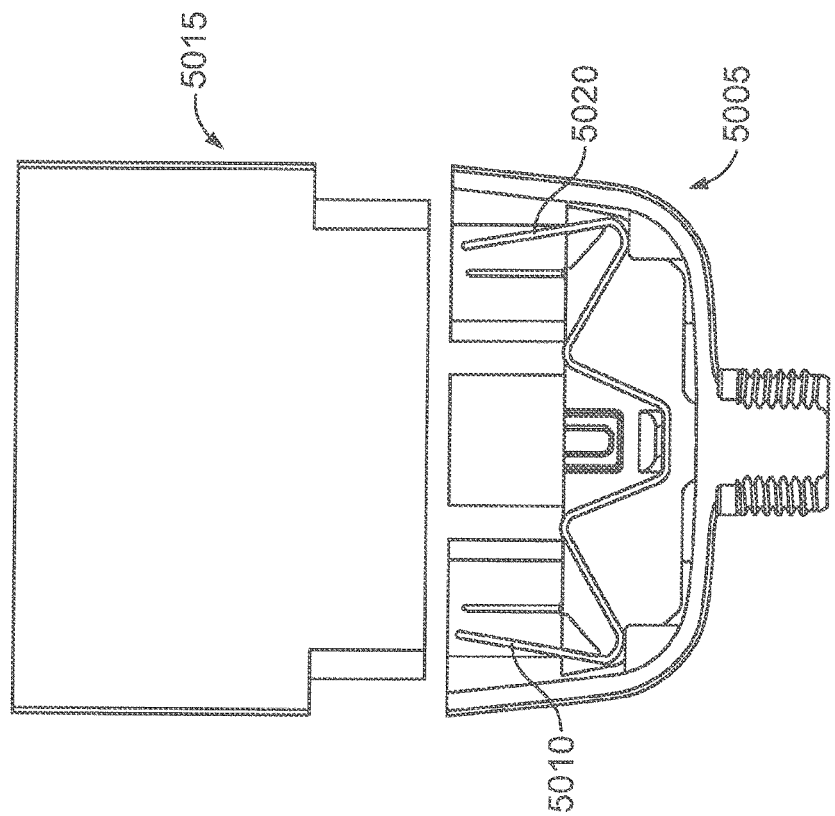
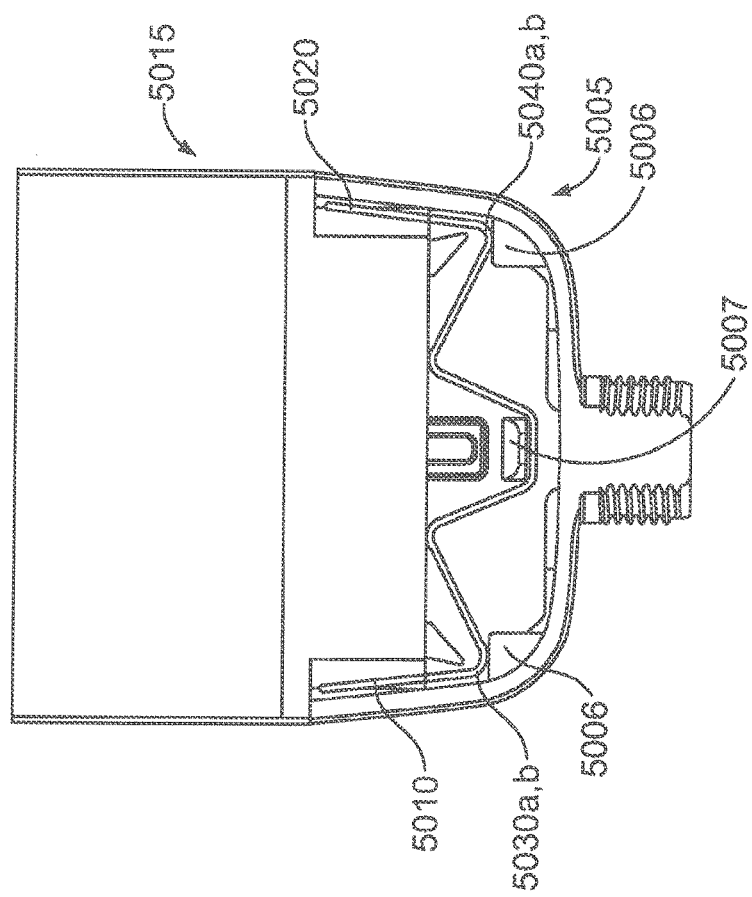

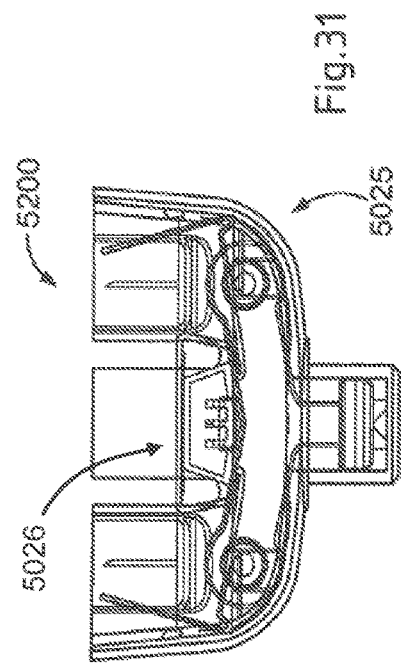
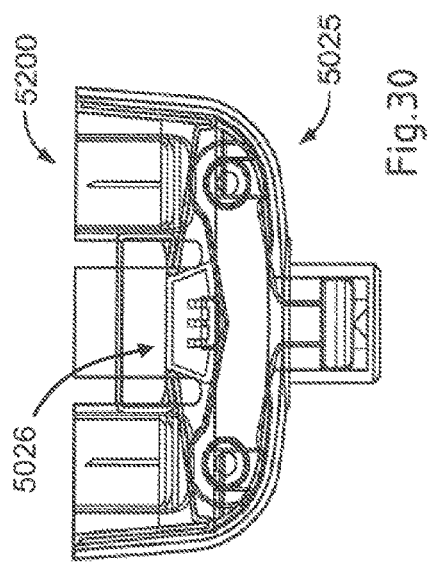
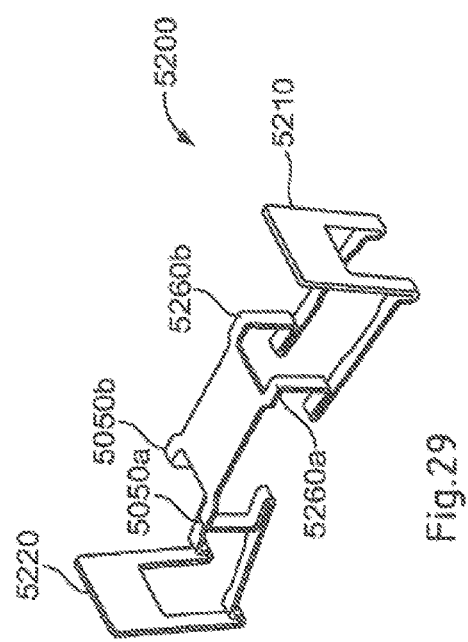

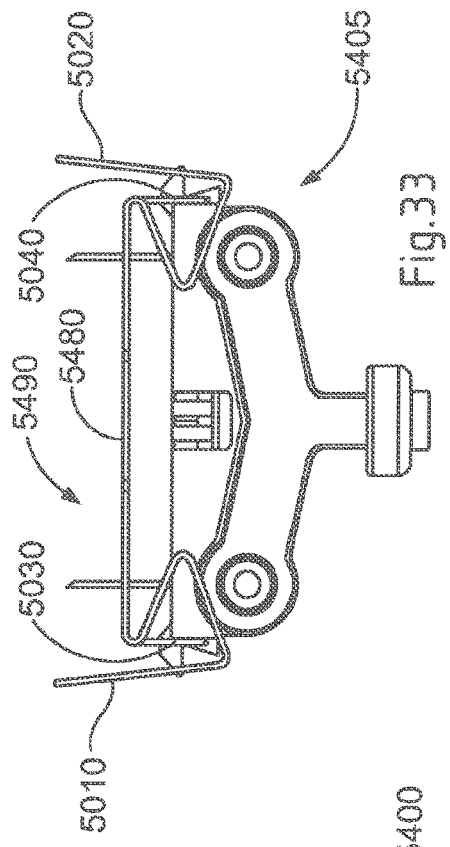
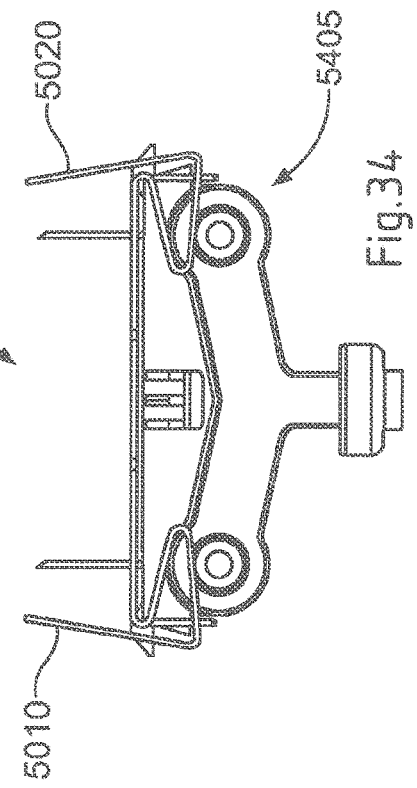
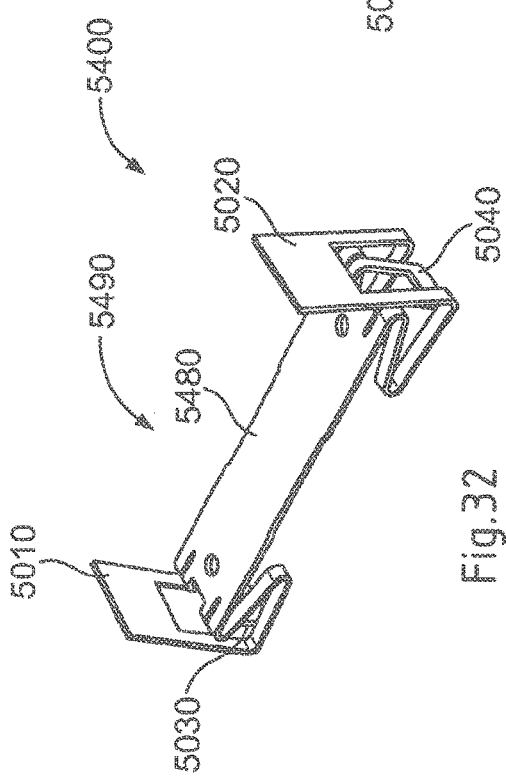
Fig. 33
Fig. 34
Fig. 32

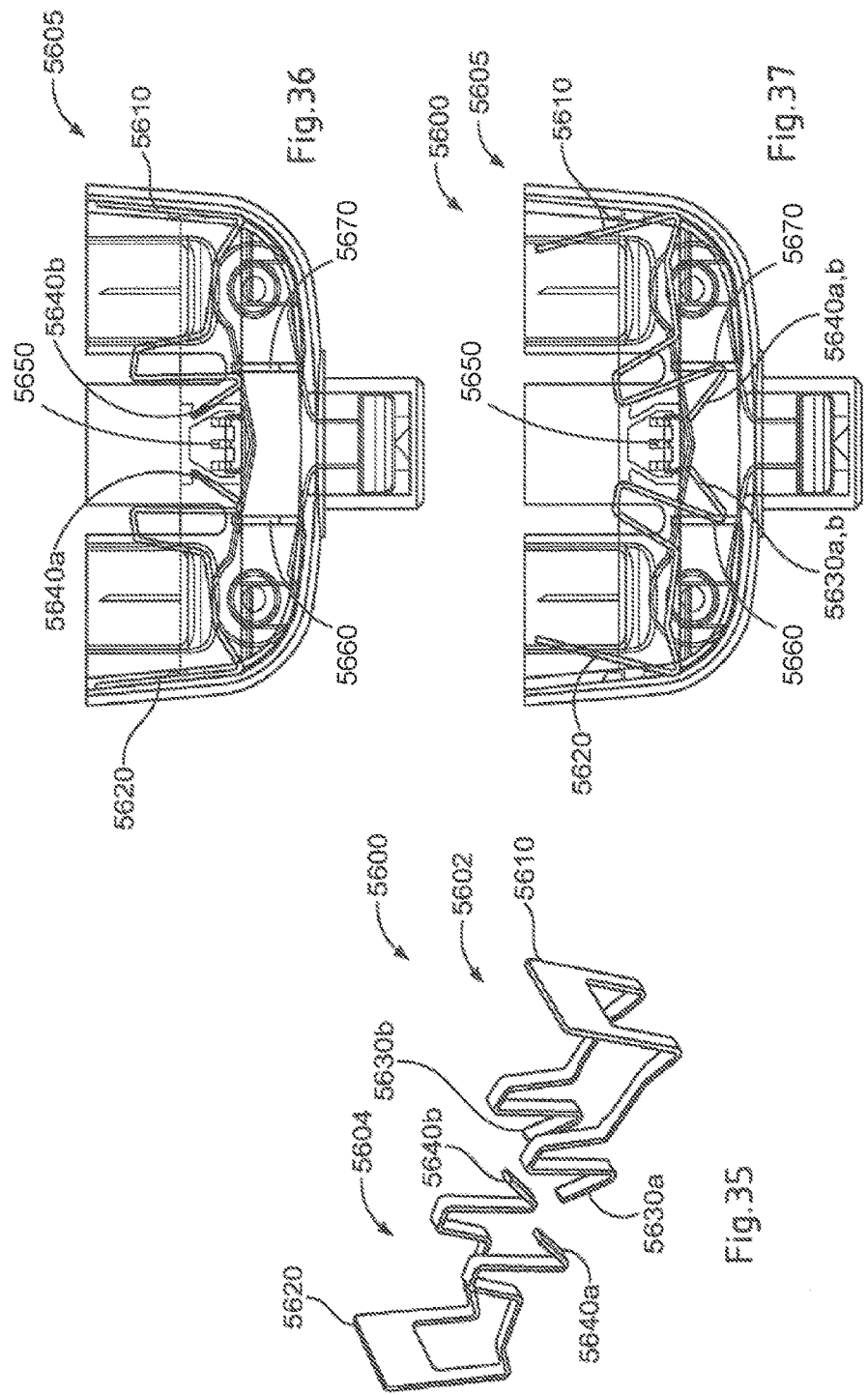

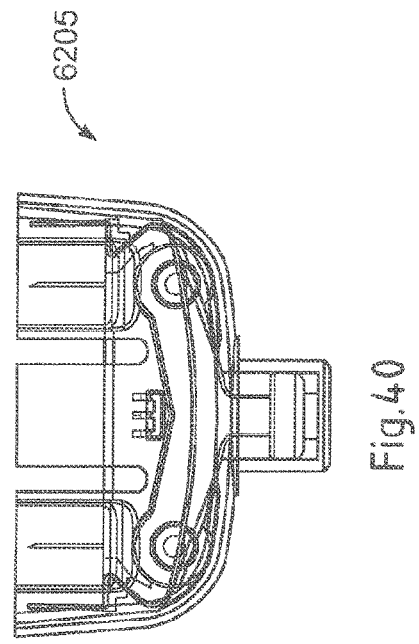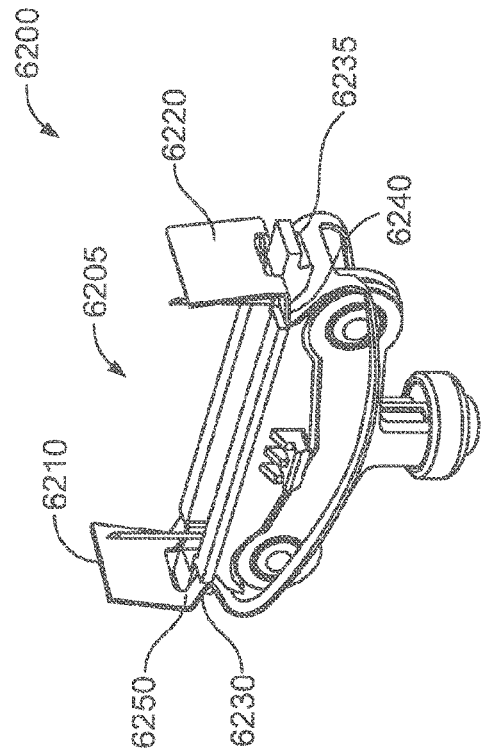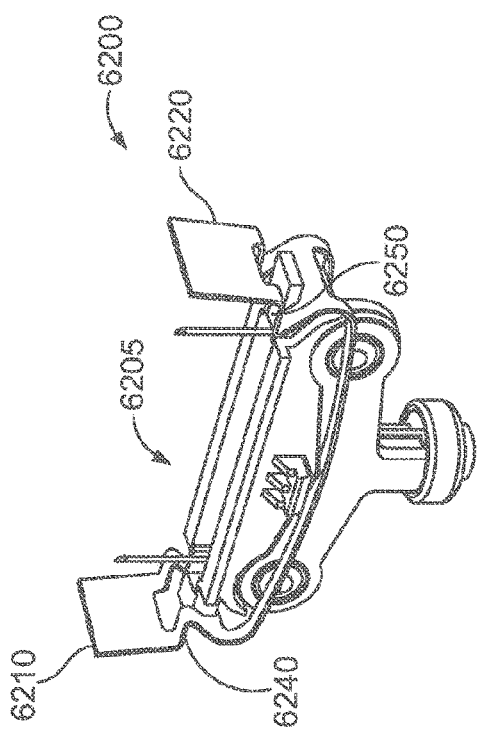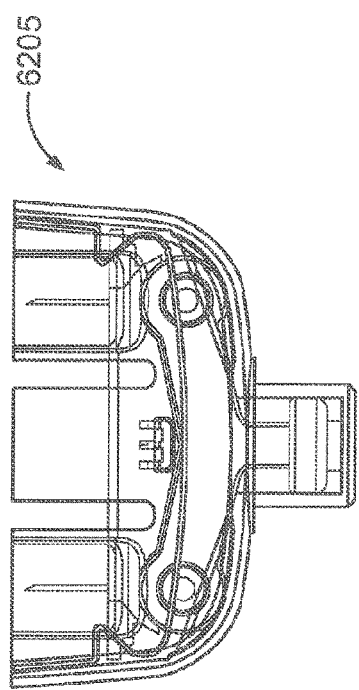

LOCKOUT ELEMENT FOR DISPENSE INTERFACE

CROSS REFERENCE TO RELATED APPLICATIONS

The present application is a U.S. National Phase Application pursuant to 35 U.S.C. § 371 of International Application No. PCT/EP2012/057692 filed Apr. 26, 2012, which claims priority to U.S. Provisional Patent Application No. 61/480,063 filed Apr. 28, 2011, and European Patent Application No. 11173278.0 filed Jul. 8, 2011. The entire disclosure contents of these applications are herewith incorporated by reference into the present application.

FIELD OF DISCLOSURE

The present patent application relates to medical devices for delivering at least two drug agents from separate reservoirs. Such drug agents may comprise a first and a second medicament. The medical device includes a dose setting mechanism for delivering the drug agents automatically or manually by the user. In particular, the present invention relates to a dispense interface comprising a lockout element for use with such a medical device.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

Delivering one or more medicaments through a dose dispenser with a dispense interface can result in the contamination of the dispense interface with traces of each medicament. This contamination may prohibit reusing the dispense interface, for example after a certain time or after a predetermined number of usages, because the purity of the delivered medicaments cannot be guaranteed. Even a user who is conscious of this problem may inadvertently try to reuse a dispense interface because he may not remember and may find it difficult or impossible to determine by inspection whether a given dispense interface has in fact been used or not.

It is therefore desirable to provide the dispense interface with a mechanism that prevents reuse of the dispense interface with a drug delivery device. This mechanism should be such that it is effective in its prevention of reuse as well as safe from manual manipulation by a user.

Thus it is an object of the invention to provide a dispense interface for use with a drug delivery device which has a lockout mechanism that prevents reusing this dispense interface after it has already been used with a drug delivery device.

This object is solved by a dispense interface for use with a drug delivery device, the dispense interface comprising a lockout element, wherein the lockout element is arranged at least partially between an outer body of the dispense interface and an inner body of the dispense interface and wherein the lockout element is maintained in a first position, wherein the lockout element in the first position is configured to move into a second position when the dispense interface is first attached and then removed from said drug delivery device, wherein the lockout element is configured to prevent said dispense interface from being reattached to a drug delivery device in the second position.

The lockout element may be a structure made of any material. The lockout element may comprise more than one separate structure. The lockout element may also be a single integral structure. The lockout element may be made of metal. In particular, the lockout element may be a spring steel wireform.

The lockout element is arranged in its default state, i.e. in its first position, such that it allows attachment of the dispense interface to the drug delivery device. However, the process of attaching the dispense interface to the drug delivery device mechanically moves the lockout element, either directly or indirectly, such that, once the dispense interface is detached and thereby is removed from the drug delivery device, the lockout element mechanically blocks a reattachment of the dispense interface to the drug delivery device. Therefore a reuse of the dispense interface is prevented and the risk of contamination from residual drug components within the dispense interface eliminated.

To this end, the lockout element is maintained in said first position in which it does not interfere with the attachment of the dispense interface to the drug delivery device. It may be that the lockout element is in a relaxed state in this first position. It may also be that the lockout element is biased to move in another position but is mechanically held back.

The lockout element is arranged at least partially between an outer body and an inner body of the dispense interface, i.e. the dispense interface is assembled by the combination of an inner body and an outer body and the lockout element is arranged at least partially in the cavity formed between those two bodies. Some parts of the lockout element may extend beyond the cavity formed in the space between the outer body and the inner body of the dispense interface.

The lockout element is arranged such that it is engaged during the attachment of the dispense interface to the drug delivery device. This engagement moves the lockout element from its first position into a second position. The change of position may also comprise a change of shape of the lockout element. In the second position of the lockout element, the lockout element blocks the re-attachment of the dispense interface to the drug delivery device. The lockout element may complete its move to the second, blocking position only after the dispense interface has been detached from the drug delivery device. Thereby the engagement may move the lockout element from a first position to a third position, in which the lockout element is biased to move into the second position but may be blocked from doing so, for example by the presence of the still-attached drug delivery device. Subsequently, the lockout element may move from this third position to the second position only after the dispense interface has been detached from the drug delivery device. Not all parts of the lockout element need to be arranged differently from one position to the next, i.e. moving from one position to another position may not comprise movement of all parts of the lockout element. It is possible that some or even most parts of the lockout element will remain in the same position when the lockout element moves from the first position to the second position or from the second position to the third position. Therefore any movement of the lockout element from one position to another may only be a partial movement.

In a preferred embodiment of the invention, the lockout element is arranged in the first position such that it is engaged by the drug delivery device on attachment of the dispense interface to the drug delivery device and moved into a third position. The engagement by the drug delivery device may be such that it moves the lockout element beyond a restraining element such that this restraining element no longer acts to block the movement of the lockout element.

In a further preferred embodiment, the lockout element is configured to move from a third position to the second position on removal of the drug delivery device from the dispense interface. It may be that the lockout element is biased to move toward the second position from the third position, for example by having internal strain in the third position. In particular, some parts of the lockout element may be bent outward in the third position and may bend inward when the drug delivery device is detached and the lockout element moves into the second position.

In yet another preferred embodiment of the invention, the lockout element comprises a spring assembly. The spring assembly may have a spring characteristic suitable for providing the bias for the lockout element to move from the third position to the second position or from the first position to the second position. The lockout element itself may form the spring assembly by having spring characteristics.

In a further preferred embodiment of the invention, the spring assembly comprises two or more sprung forms.

In an additional embodiment of the invention, the spring assembly comprises at least one rigid component.

In a preferred embodiment of the invention, the lockout element comprises at least one knuckle portion configured to be contacted by the drug delivery device on attachment of the dispense interface to the drug delivery device, comprises at least one wing portion and comprises a pivot point for each wing portion, wherein each wing portion is configured to bend inward around the respective pivot point when the lockout element moves to the second position. In particular, the drug delivery device may engage the lockout element at the at least one knuckle portion. Each wing portion may be prevented from bending inward as long as the dispense interface is attached to the drug delivery device. In particular, each wing portion may be prevented from bending inward when the lockout element is in the third position. On detachment of the dispense interface from the drug delivery device, the lockout element may move into the second position by each wing portion bending inward. By bending inward, each wing portion may move into the path of the drug delivery device for attachment to the dispense interface, thereby preventing reattachment to the dispense interface.

In a further preferred embodiment of the invention, the dispense interface comprises a retention arrangement configured to maintain the lockout element in the first position until the lockout element is engaged by the drug delivery device on attachment of the dispense interface to the drug delivery device.

In yet a further preferred embodiment of the invention, the retention arrangement comprises at least one stepped feature on the inner body of the dispense interface. The stepped feature may hold the lockout element in the first position and may allow movement of the lockout element only into the direction of the second or third position. The lockout element in the first position is configured to be pushed away from the at least one stepped feature on attachment of the dispense interface to the drug delivery device.

In yet another embodiment of the invention, the retention arrangement comprises a deformable section, which deformable section is configured to be deformingly engaged by the drug delivery device on attachment of the dispense interface to the drug delivery device such that the lockout element is moved away from the first position. Being deformingly engaged by the drug delivery device may mean that the deformable section is deformed by being engaged by the drug delivery device. As a consequence of being deformed, the retention arrangement no longer retains the lockout element in the first position.

In a further preferred embodiment of the invention, the dispense interface comprises a retention arrangement configured to maintain the lockout element in the second position. When the lockout element is in the first position, it may be moved into the second position on attachment of the dispense interface to the drug delivery device. For example, the lockout element may be pushed by the drug delivery device in the second position. In this embodiment, the lockout element is biased to move away from the second position but is maintained in the second position by the retention arrangement configured to prevent the lockout element from changing its position. Thus, the lockout element is in an unbiased and therefore relaxed state in the first position, and it is forcibly moved into a strained, second position.

In another embodiment of the invention, the retention arrangement comprises at least one non-return clip configured to maintain the lockout element in the second position and wherein a clip portion of the lockout element is configured to ride over the at least one non-return clip when it is moved into the third position. The non-return clip may be a ramping protrusion arranged on the inner body of the dispense interface. The non-return clip may be configured to allow movement of a clip portion of the lockout element across the non-return clip in a distal direction but prevent movement back across the non-return clip in the proximal direction. Thus, the clip portion of the lockout element may not change its position when the lockout element moves from the third position to the second position.

In a further preferred embodiment of the invention, the retention arrangement comprises at least one retention region which is ramped and then steps back to a flat region in a distal direction of the dispense interface, which at least one retention region is arranged on the inner body of the dispense interface and which at least one retention region is configured to engage the lockout element symmetrically on at least two surfaces of contact in the second position. The retention region may be a protrusion which is shaped to permit movement of the lockout element into the second position when the lockout element is engaged by the drug delivery device and further shaped to maintain the lockout element in the second position.

In a preferred embodiment of the invention, the lockout element comprises a set of legged wings at each end of the lockout element facing in a proximal direction and further comprises a tab at each end of the lockout element facing in a distal direction, wherein each respective tab is arranged between the corresponding set of wings and wherein the lockout element comprises a platform region configured to be engaged by the drug delivery device on attachment of the dispense interface to the drug delivery device.

In yet another preferred embodiment of the invention, the lockout element comprises two symmetrical spring forms, wherein each spring form comprises a hooked end, wherein the retention arrangement comprises at least one boss feature on the inner body of the dispense interface and further comprises at least one rib on the outer body of the dispense interface, wherein a boss feature and a corresponding rib are arranged to provide a gap in between and wherein each hooked end is configured to move through the gap between a boss feature and a corresponding rib when the lockout element is engaged by the drug delivery device on attachment of the dispense interface to the drug delivery device.

BRIEF DESCRIPTION OF THE FIGURES

These as well as other advantages of various aspects of the present invention will become apparent to those of ordinary skill in the art by reading the following detailed description, with appropriate reference to the accompanying drawings, in which:

FIG. 27 illustrates a cross-sectional view of the alternative locking member illustrated in FIGS. 24-25 with the dispense interface mounted onto a distal end of a drug delivery device;

FIG. 28 illustrates a cross-sectional view of the alternative locking member illustrated in FIGS. 24-25 in a locked condition after the dispense interface has been removed from the distal end of a drug delivery device;

FIG. 29 illustrates a perspective view of an alternative arrangement of a locking member for use with a dispense interface;

FIG. 30 illustrates a cross-sectional view of the locking member illustrated in FIG. 29 within a dispense interface with the locking member in a receptive condition;

FIG. 31 illustrates a cross-sectional view of the locking member illustrated in FIG. 29 within a dispense interface with the locking member in a locked condition;

FIG. 32 illustrates a perspective view of an alternative arrangement of a locking member for use with a dispense interface;

FIG. 33 illustrates a side view of the locking member illustrated in FIG. 32 within a dispense interface with the locking member in a receptive condition;

FIG. 34 illustrates a side view of the locking member illustrated in FIG. 32 within a dispense interface with the locking member in a locked condition;

FIG. 35 illustrates a perspective view of an alternative arrangement of a locking member for use with a dispense interface;

FIG. 36 illustrates a cross-sectional view of the locking member illustrated in FIG. 35 within a dispense interface with the locking member in a receptive condition;

FIG. 37 illustrates a cross-sectional view of the locking member illustrated in FIG. 35 within a dispense interface with the locking member in a locked condition;

FIG. 38 illustrates a perspective view of an alternative arrangement of a locking member for use with a dispense interface;

FIG. 39 illustrates a cross-sectional view of the locking member illustrated in FIG. 38 within a dispense interface with the locking member in a receptive condition;

FIG. 40 illustrates a cross-sectional view of the locking member illustrated in FIG. 38 within a dispense interface with the locking member in an activated condition;

FIG. 41 illustrates a perspective view of the locking member illustrated in FIG. 38 within a dispense interface with the locking member in a locked condition;

DETAILED DESCRIPTION

Figure 1:
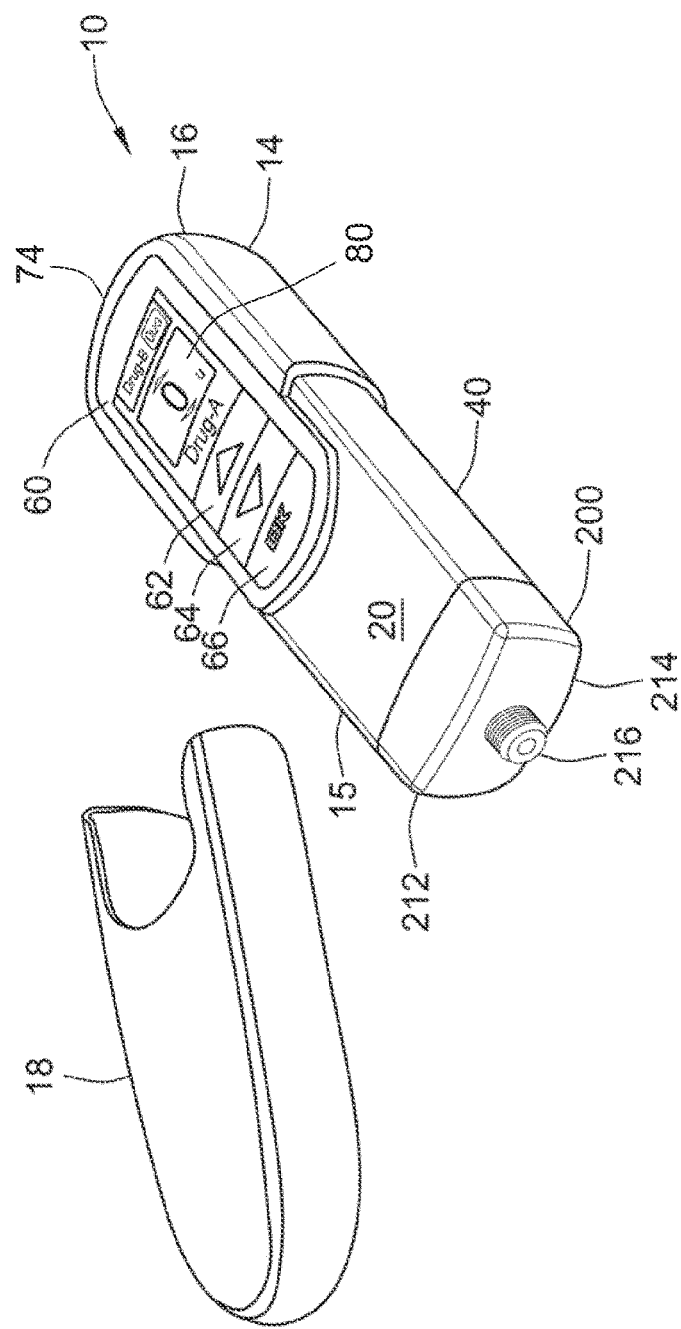
FIG. 1 illustrates a perspective view of a delivery device with an end cap of the device removed.
Figure 2:
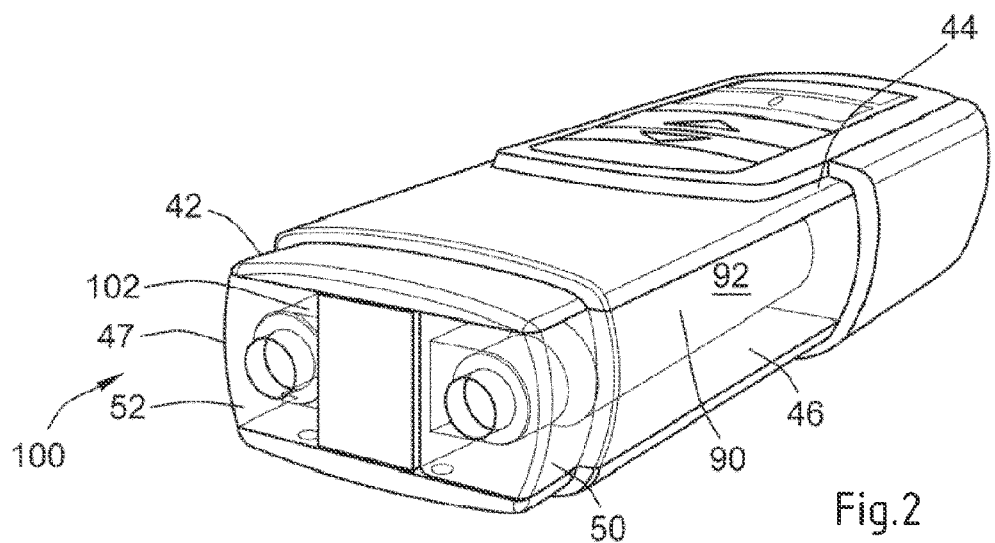
FIG. 2 illustrates a perspective view of the delivery device distal end showing the cartridge.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
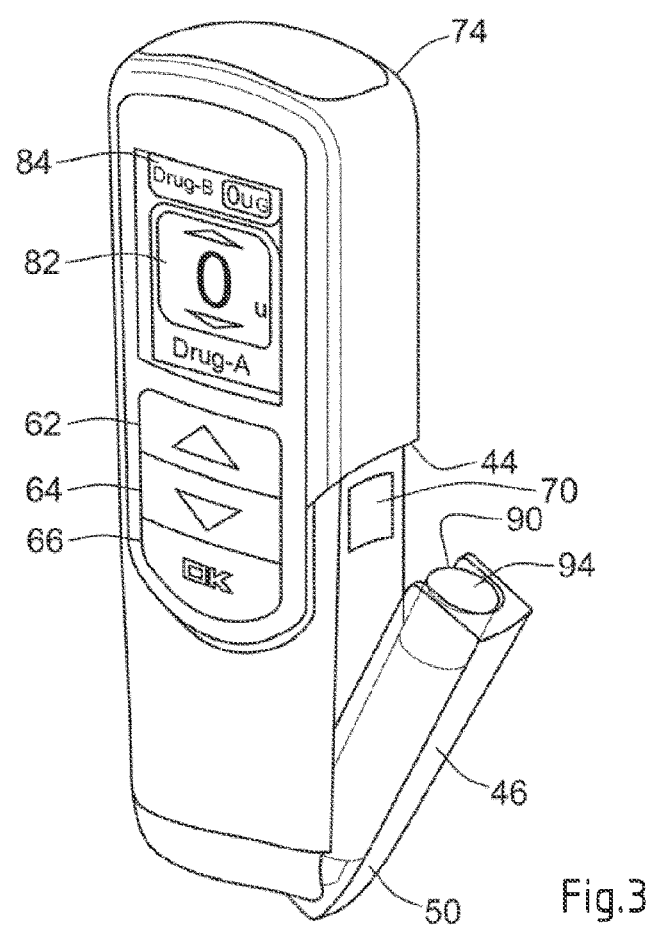
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
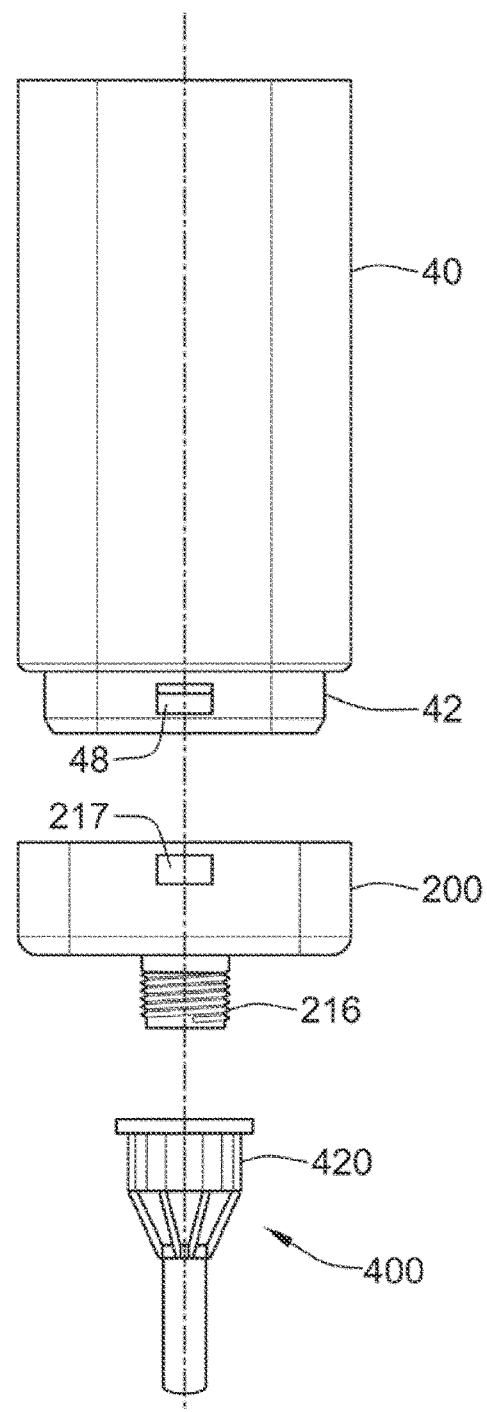
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
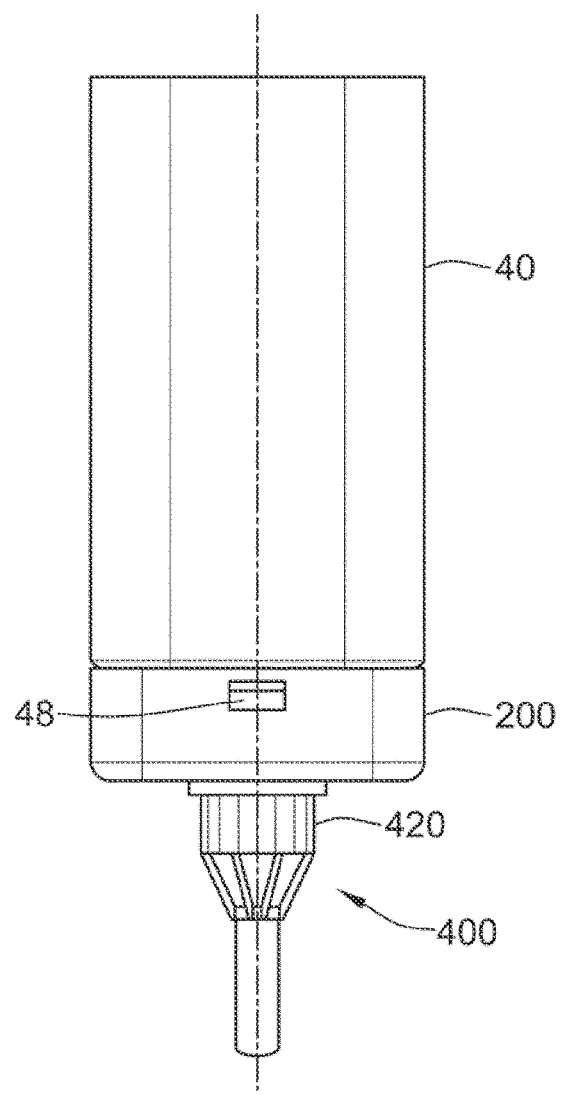
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
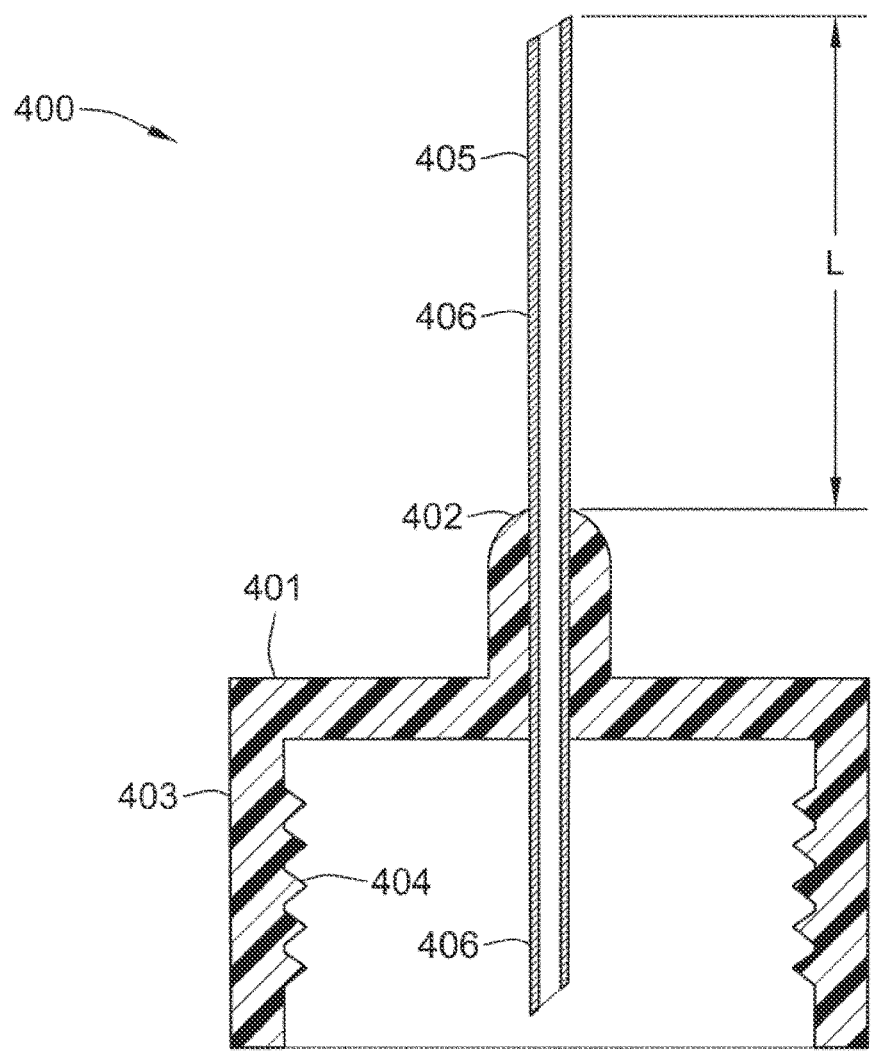
FIG. 6 illustrates one arrangement of needle assembly that may be mounted on a distal end of the delivery device.
Figure 7:
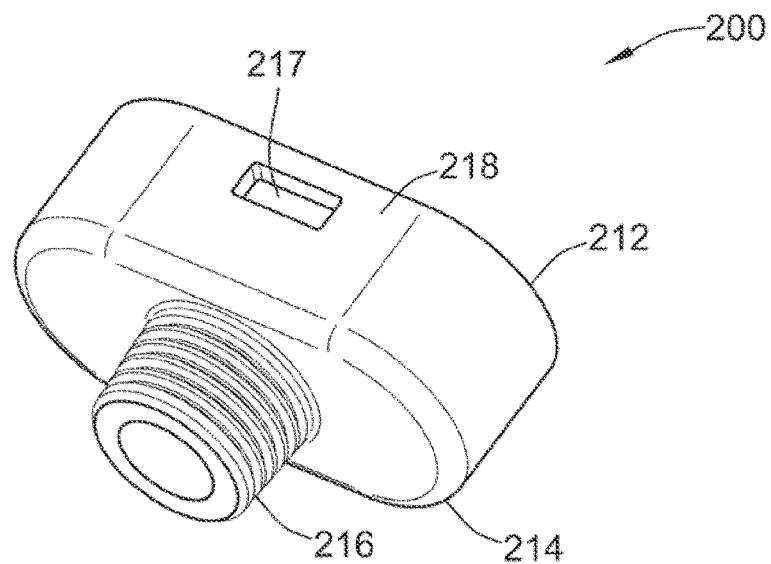
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
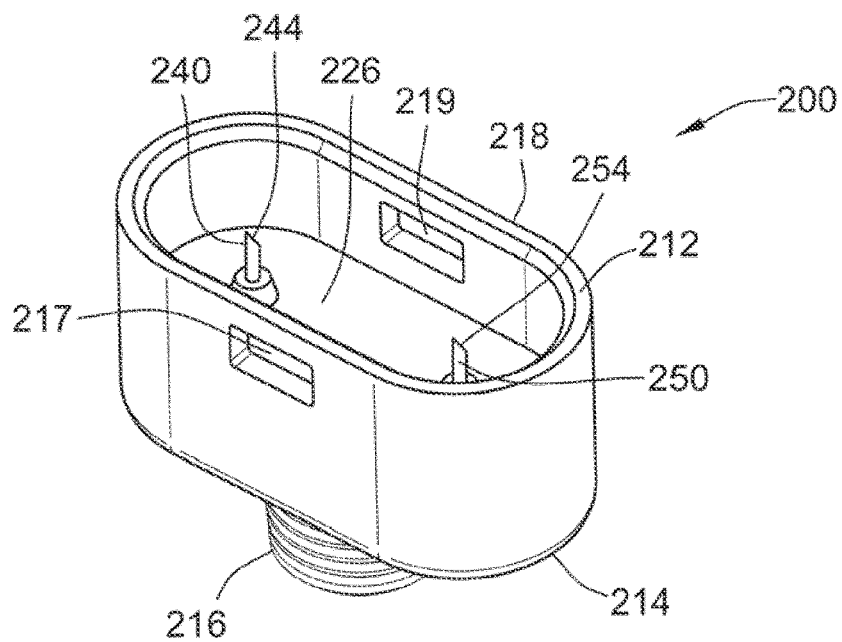
FIG. 8 illustrates another perspective view of the dispense interface illustrated in FIG. 4.
Figure 9:
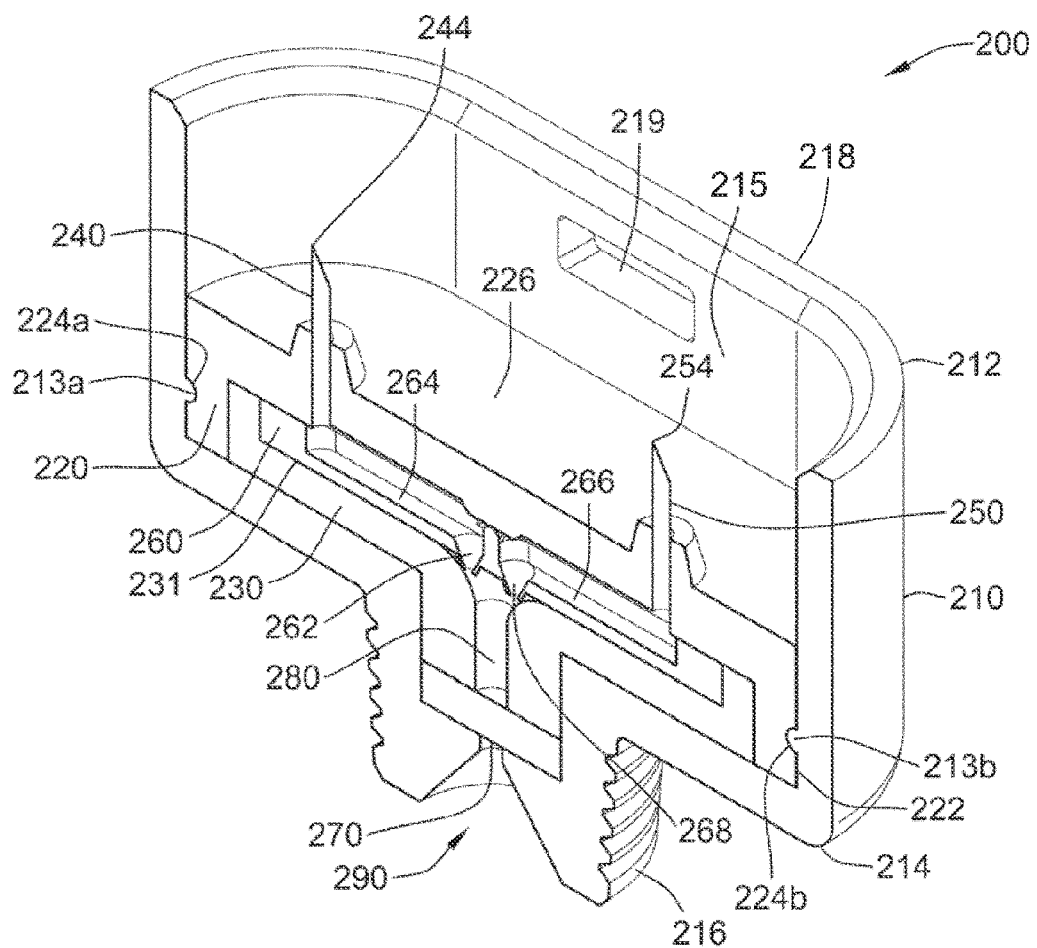
FIG. 9 illustrates a cross-sectional view of the dispense interface illustrated in FIG. 4.
Figure 10:
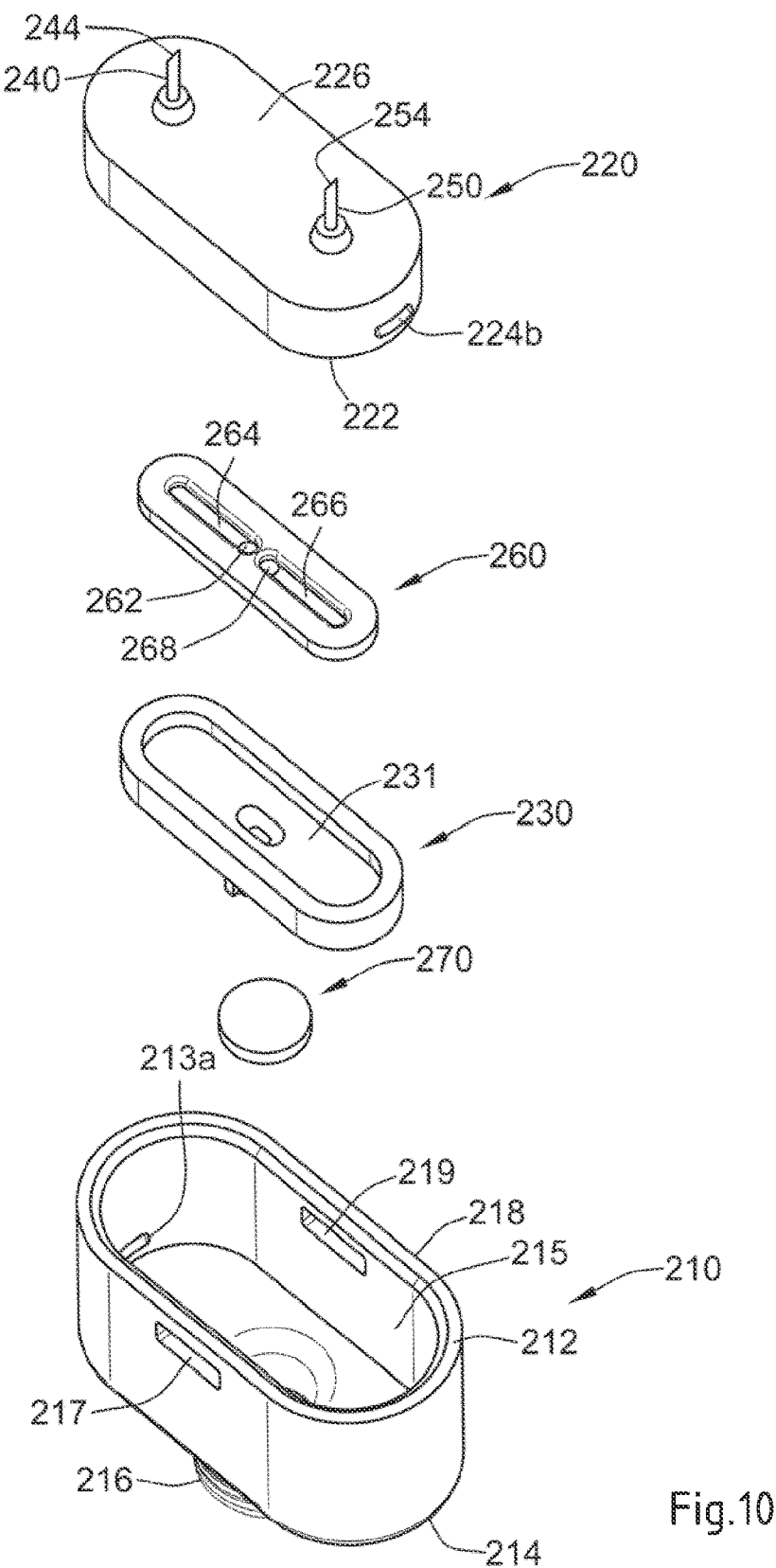
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
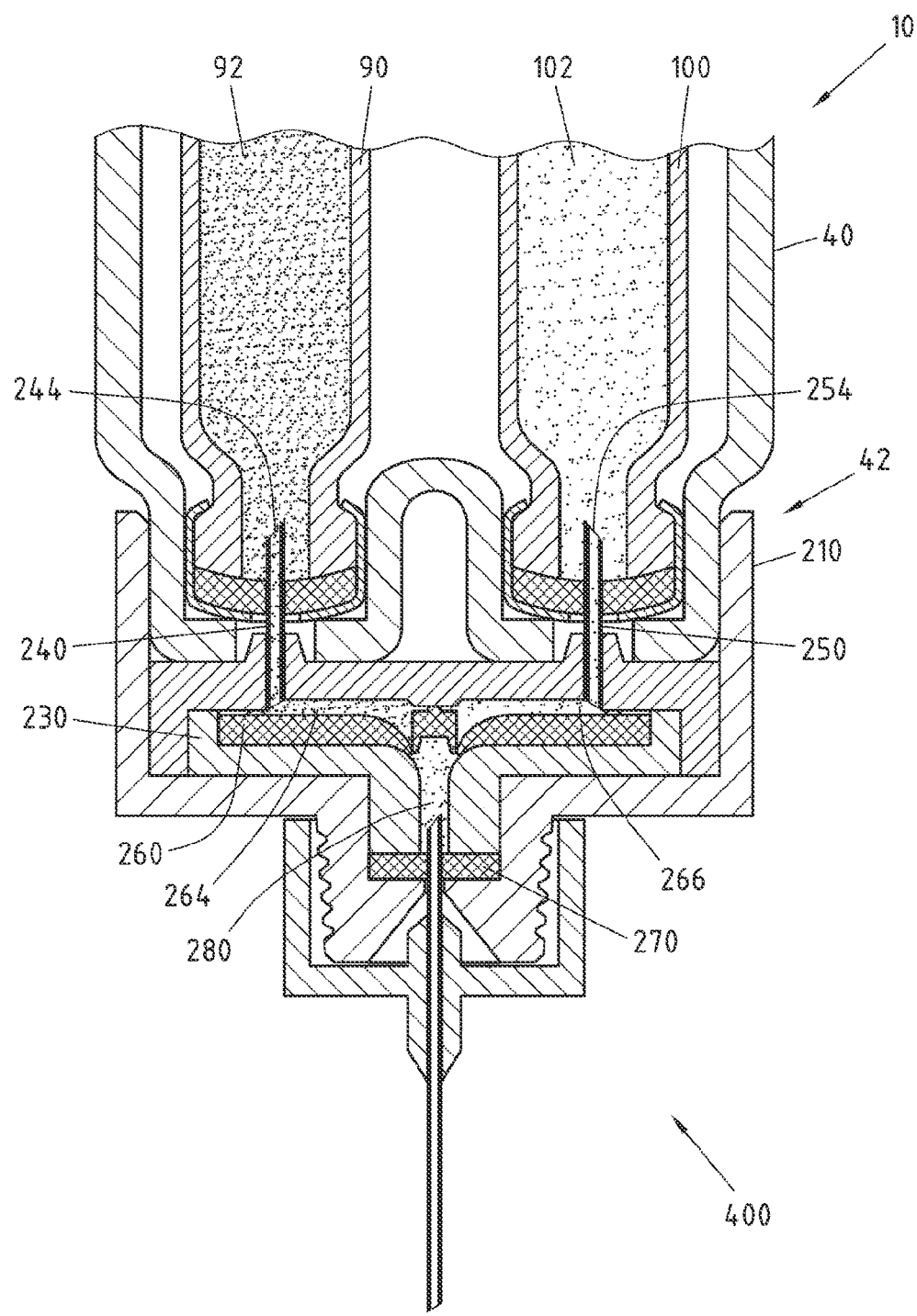
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

In the following embodiments of the present invention will be described in detail with reference to FIGS. 12 to 45.

Figure 12:
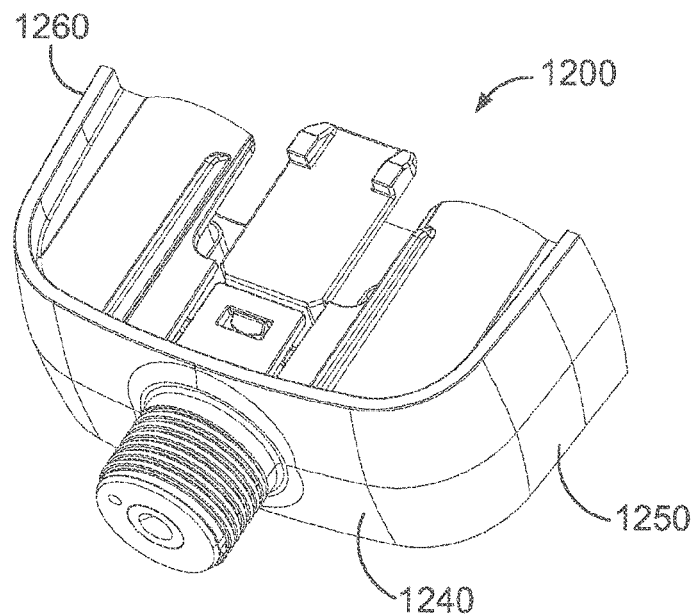
FIG. 12 illustrates a perspective view of a dispense interface.
Figure 13:
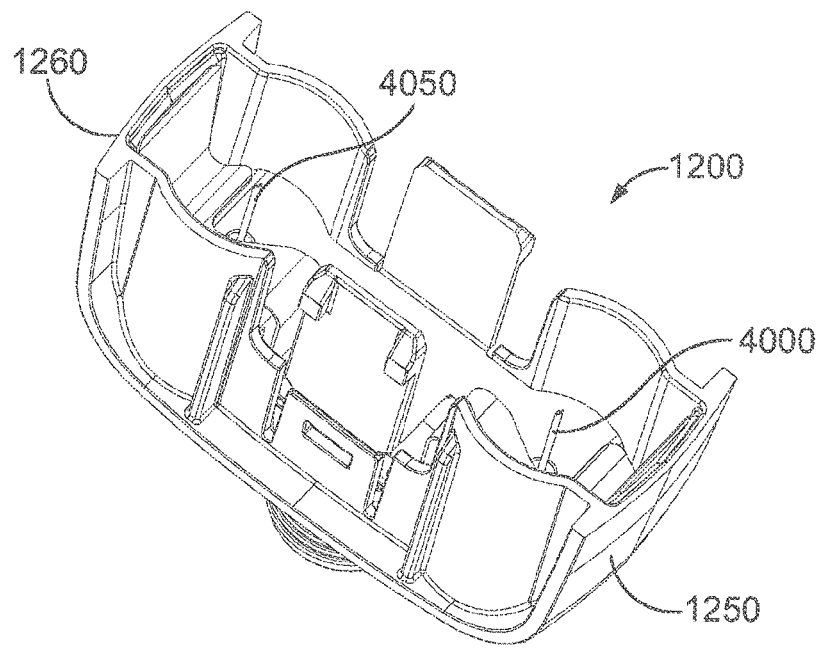
FIG. 13 illustrates another perspective view of the dispense interface illustrated in FIG. 12.
Figure 14:
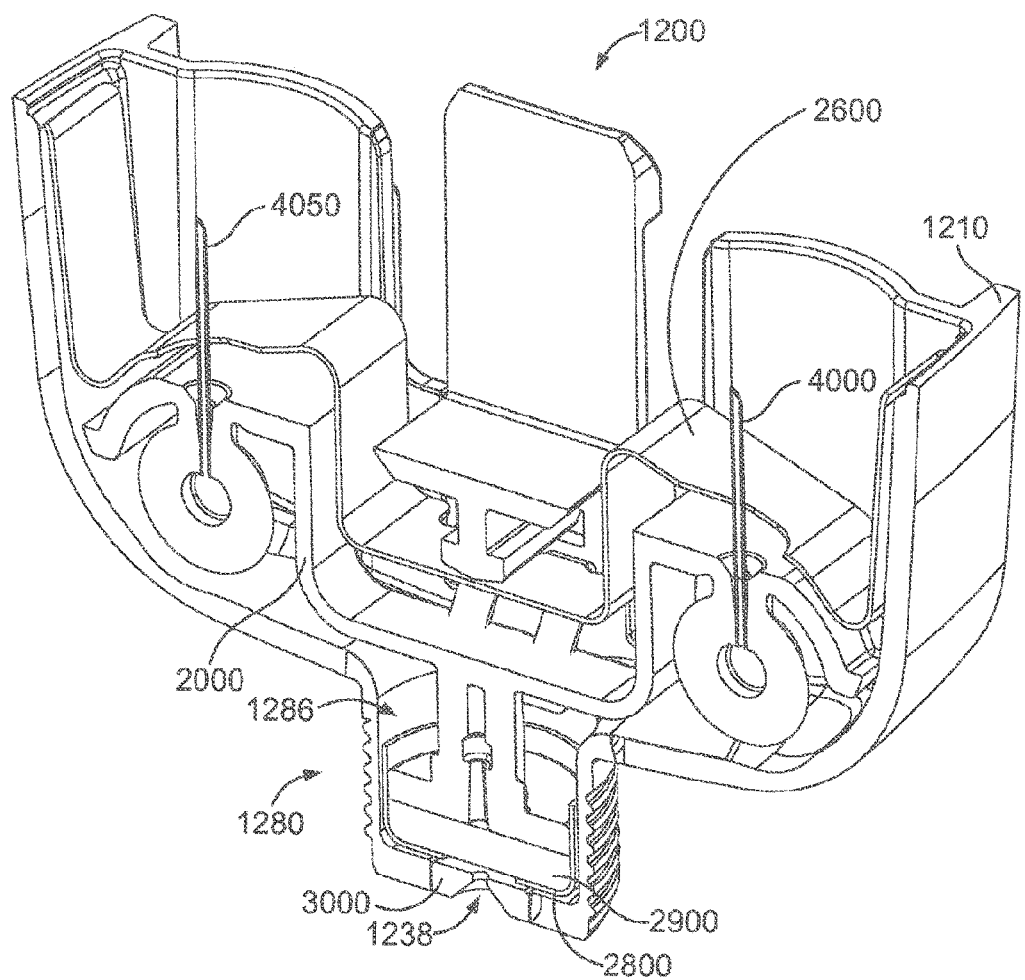
FIG. 14 illustrates a cross sectional view of the dispense interface illustrated in FIG. 12-13.

FIG. 12 illustrates a perspective view on the distal end of one example embodiment of the dispense interface 1200. FIG. 13 illustrates a perspective view on the proximal end of the example embodiment of the dispense interface 1200 illustrated in FIG. 12 and FIG. 14 illustrates a cross-sectional view of the dispense interface 1200 illustrated in FIGS. 12 and 13. As will now be discussed in greater detail, in one preferred arrangement, the dispense interface 1200 illustrated in FIGS. 12-14 comprises:

a. a main outer body 1210;
b. an inner body 2000;
c. a manifold 2300;
d. a first piercing needle 4000;
e. a second piercing needle 4050;
f. a lock-out spring 2600;
g. a first diaphragm valve 2700;
h. a second diaphragm valve 2750;
i. a ferrule 2800;
j. an outer septum 2900; and
k. a needle guide 3000.

Figure 15:
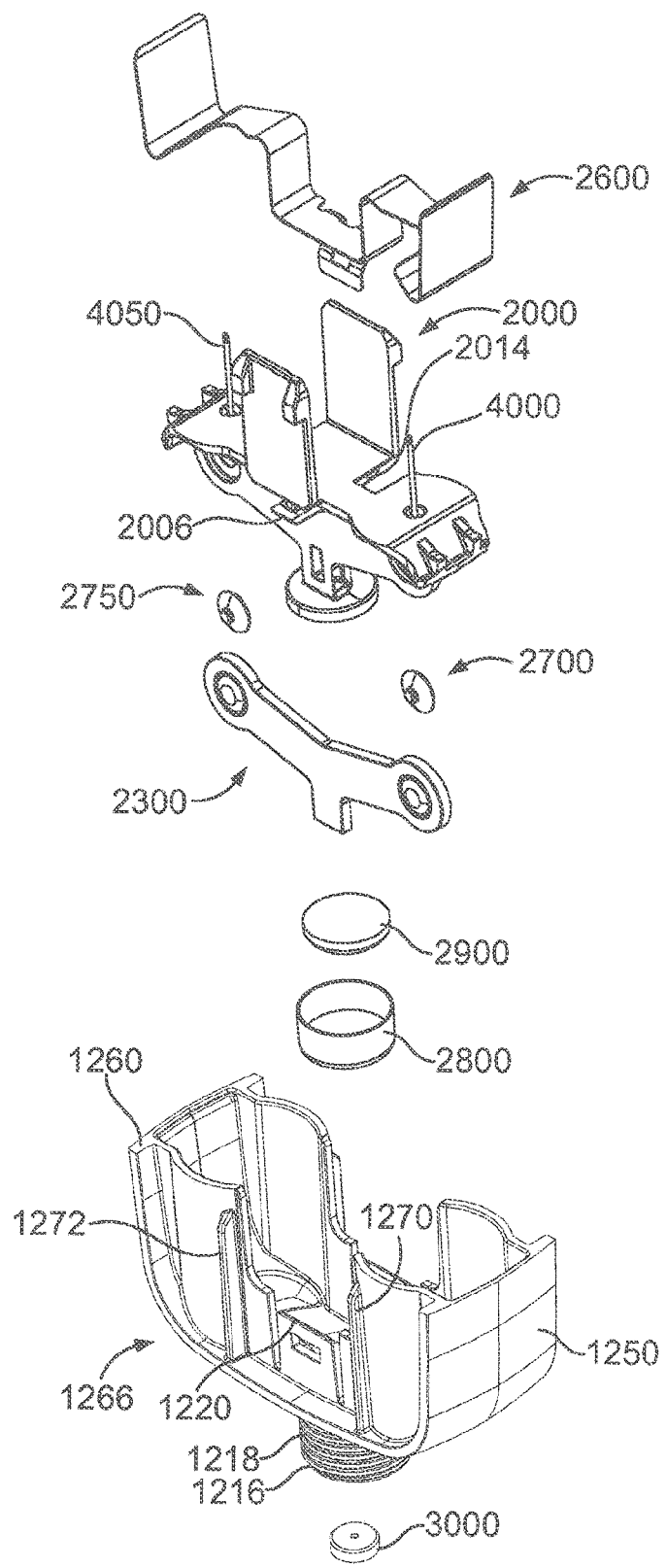
FIG. 15 illustrates an exploded view of the dispense interface illustrated in FIG. 12-13.
Figure 16:
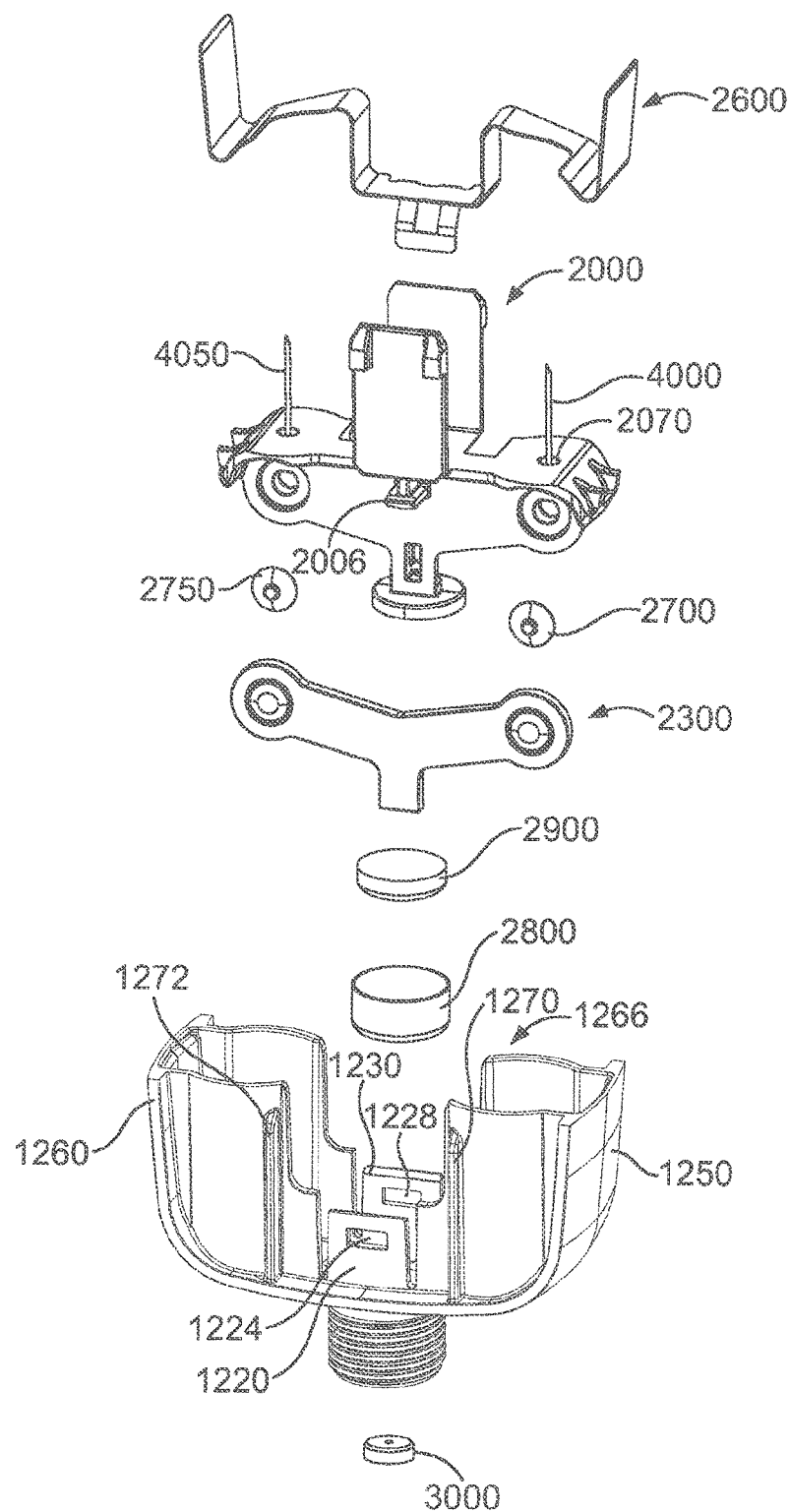
FIG. 16 illustrates an alternative exploded view of the dispense interface illustrated in FIG. 12-13.

A general interrelationship between these various component parts may be seen from FIG. 15 which illustrates one exploded perspective view of the dispense interface 1200. Similarly, FIG. 16 illustrates an alternative exploded perspective view of the dispense interface 1200.

Figure 17:
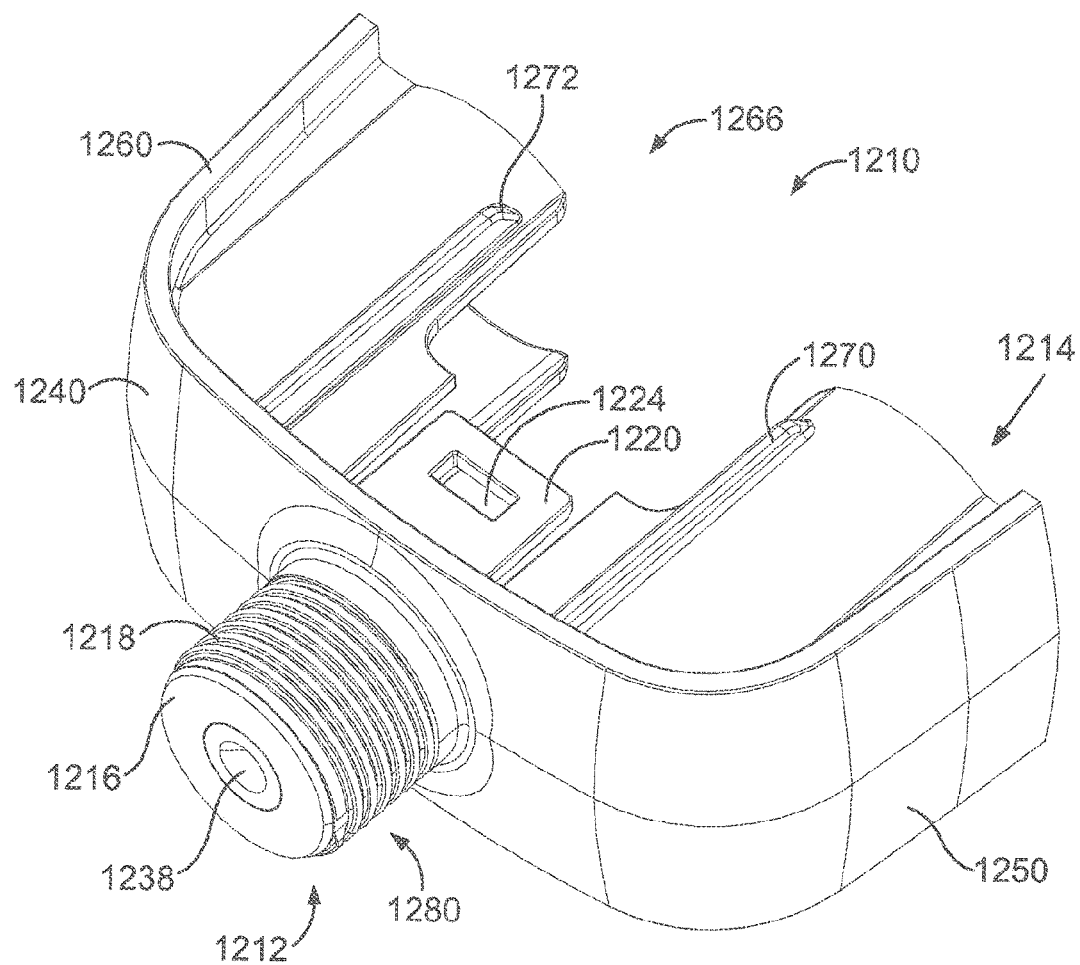
FIG. 17 illustrates a perspective view of a main outer body of the dispense interface illustrated in FIG. 15-16.

FIG. 17 illustrates a perspective view of the main outer body 1210 of the dispense interface 1200. Referring now to FIGS. 12-17, as illustrated, this body 1210 comprises a main body distal end 1212 and a main body proximal end 1214. The main body proximal end 1214 is configured to be seated along the distal end of the drug delivery device near the distal end of the cartridge holder. Preferably, the main outer body 1210 comprises an injection molded polypropylene (PP) component.

Furthermore, the main body 1210 comprises a first and a second shroud 1250, 1260 extending from the distal end to the proximal end of the main body 1210. Preferably when the main body is assembled together with the other components of the dispense interface 1200 and the interface is attached to the drug delivery device, shrouds 1250, 1260 obscure the exposed first and second piercing needles or cannulas 4000, 4050 (see, also, e.g., FIG. 13). As such, shrouds 1250, 1260 help to prevent needle stick injuries as a user attaches the dispense interface 1200 to the drug delivery device 1150.

As may be seen from FIGS. 12-17, a top surface 1240 of the outer body 1210 may comprise a smooth, rounded outer surface.

In addition and now referring to FIGS. 15-17, the main outer body 1210 further comprises two flexible connecting members 1220, 1230, one on each side of the outer body 1210. For example, the first connecting member 1220 may be seen in FIGS. 15 to 17 and the second connecting member 1230 may be seen in FIG. 16. These connecting members are positioned between the first and second shrouds 1250, 1260. Preferably, these connecting members 1220, 1230 are configured as flat tabs and constructed so as to flex outwardly (i.e., away from one another) so as allow the main outer body 1210 to be attached to and disconnected from an inner body 2000 (see, e.g., FIG. 14) of the dispense interface 1200. In one example embodiment, the two connecting members 1220, 1230 extend in a proximal direction with each flat portion comprising at least one recess. For example, as may be seen from FIG. 17, the first extending flat portion 1220 comprises at least a first recess 1224. Similarly, as may be seen from FIG. 16, the second extending flat portion 1230 comprises a second recess 1228.

Preferably, the two recesses 1224, 1228 are positioned within this main outer body 1210 so as to cooperate with a first and a second outwardly protruding members 2006, 2014 respectively, located near a middle portion of the inner body 2000. For example, the inner body 2000 comprises a first outwardly protruding member 2006. A second similar outwardly protruding member 2014 is provided on the opposite side of the inner body portion. These outwardly protruding members 2006, 2014 of the inner body may be seen in FIG. 15.

As such, when the main body 1210 is axially positioned over the distal end of the inner body 2000 during an assembly step, the outwardly protruding members 2006, 2014 cooperate with the first and the second recess 1224, 1228 of the main outer body so as to form an interference fit, form fit, or snap lock between the two components. Preferably, such an interference fit comprises a permanent interference fit. Alternatively, and as those of skill in the art will recognize, other similar connection mechanisms that allow for the main outer body 1210 and the inner body 2000 to be axially coupled could be used as well. However, in one preferred arrangement, this connection comprises a permanent interference fit so as to prevent user manipulation of the interface in an attempt to reuse the dispense interface.

The inner body 2000 and a release button provided at the distal end of the cartridge holder of the device act to form an axially engaging snap lock or snap fit arrangement that could be axially slid onto the distal end of the cartridge housing. In an example embodiment, the dispense interface 1200 may be provided with a coding feature so as to prevent inadvertent dispense interface cross use. That is, the inner body of the hub could be geometrically configured so as to prevent an inadvertent cross use of one or more dispense interfaces.

The outer main body 1210 further comprises a guide arrangement 1266 preferably in the form of a plurality of guide ribs. The guide arrangement improves ease of fitment of the dispense interface 1200 onto the drug delivery device by properly orientating the interface 1200 during attachment. For example, as illustrated in FIGS. 15-17, two guide ribs 1270, 1272 are shown and they are provided along one side of the main body. The first guide rib 1270 is positioned between the first flat tab 1220 and the first shroud 1250. Similarly, the second guide rib 1272 is also positioned on the same side of the main body as the first rib 1270 and positioned between the first flat tab 1220 and the second shroud 1260. A similar dual guide rib arrangement is provided on the other side of the main body 1210, as shown in FIG. 15.

In this configuration, the guide rib arrangement improves ease of fitment. In one preferred arrangement, the guide rib arrangement 1266 may comprise a symmetric guide rib arrangement, so that the dispense interface may be fitted onto the distal end of the device in either orientation. In an alternative guide rib arrangement 1266, the arrangement comprises a non-symmetric arrangement where the dispense interface would not fit in either orientation to the drug delivery device.

Referring back to the main outer body 1200 illustrated in FIG. 17, a mounting hub 1216 is provided at the distal end 1212 of the main outer body 1210. Such a mounting hub 1216 may comprise a connecting mechanism 1218. Preferably, this connecting mechanism 1218 allows a needle assembly (such as the double ended needle assembly 400 illustrated in FIG. 6) to be releasably connected to the hub 1216. As just one example, this connecting mechanism 1218 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The main body mounting hub 1216 extends distally away from the outer surface 1240 of the outer body and may be generally shaped as a cylindrical extension 1280. This cylindrical extension 1280 defines an interior space 1286. This interior space 1286 may be seen from FIG. 14 which provides a cross sectional view of an assembled dispense interface 1200. At its most distal end, the connecting hub defines an aperture 1238.

Figure 18:
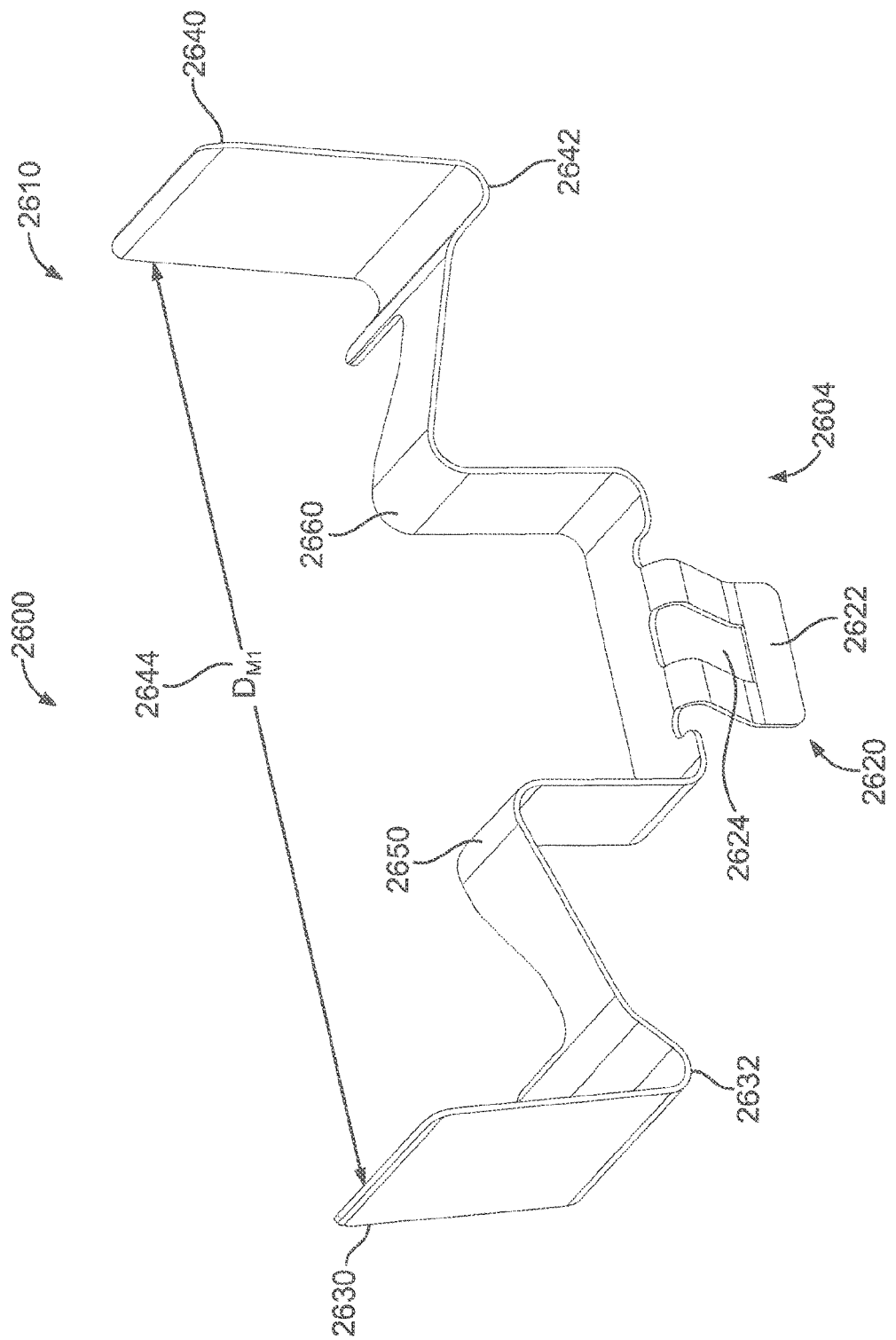
FIG. 18 illustrates a perspective view of a spring lock-out of the dispense interface illustrated in FIG. 15-16.

As may be seen from the two exploded views of the dispense interface provided in FIGS. 15 and 16, the dispense interface 2000 further comprises a dispense interface lockout element in the form of a lockout spring 2600. FIG. 18 illustrates a perspective view of such one arrangement of such a lock out member 2600 in an initial, unbiased or unstressed state. One reason that a lock out member may be incorporated into a dispense interface, such as the interface 1200 illustrated in FIG. 12, is to ensure that once the dispense interface is removed from the drug delivery device, the dispense interface cannot be re-attached and used a second time. Preventing re-attachment may ensure that medicament is not allowed to reside in the dispense interface 1200 indefinitely and contaminate the drug delivered to the patient.

Figure 19:
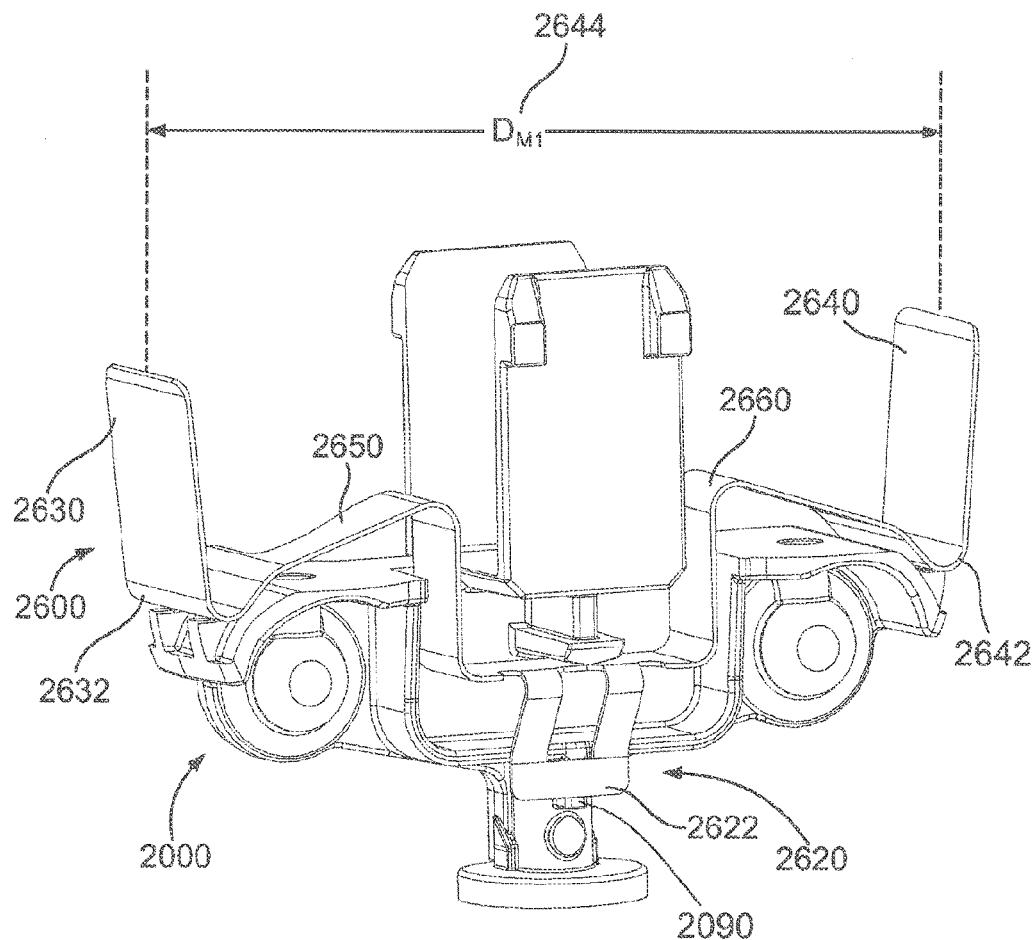
FIG. 19 illustrates a perspective view of a spring lock-out illustrated in FIG. 18 in a first position.

FIG. 19 illustrates a perspective view of one arrangement of the dispense interface lock out spring 2600 illustrated in FIG. 18 seated on the inner body 2000. In this illustrated arrangement, the lock out spring resides in a first or an initial position. As illustrated, the lock out spring 2600 extends from a distal spring end 2604 to a proximal spring end 2620. Near its distal end 2604, the lock out spring 2600 comprises a spring tip 2620. This spring tip 2620 comprises a tab 2622 defining a recess 2624.

Near its proximal end 2610, the lock out spring 2600 comprises a first spring arm 2630 and a second spring arm 2340. For example, the first spring arm 2630 extends proximally from a first pivot point 2632 of the spring 2600. Similarly, the second spring arm 2340 extends proximally from a second pivot point 2642 of the spring 2600. In the initial spring position illustrated in FIG. 18, both the first and the second spring arms 2630, 2640 reside in an unstressed state. That is, both arms flex radially outward, away from one another a spaced amount defining an initial distance DM1 2644 of a mouth created between the first and the second spring arm 2630, 2640. As will be described in detail below, when the spring 2600 is placed within a stressed state (so as to lock out the spring preventing re-attachment), the first and second spring arms 2630, 2640 flex towards one another at the first and second pivot points 2632, 2642, respectively. This flexing causes the arms 2630, 2640 to reduce the initial distance DM1 of the mouth to a smaller second mouth distance DM2.

Figure 20:
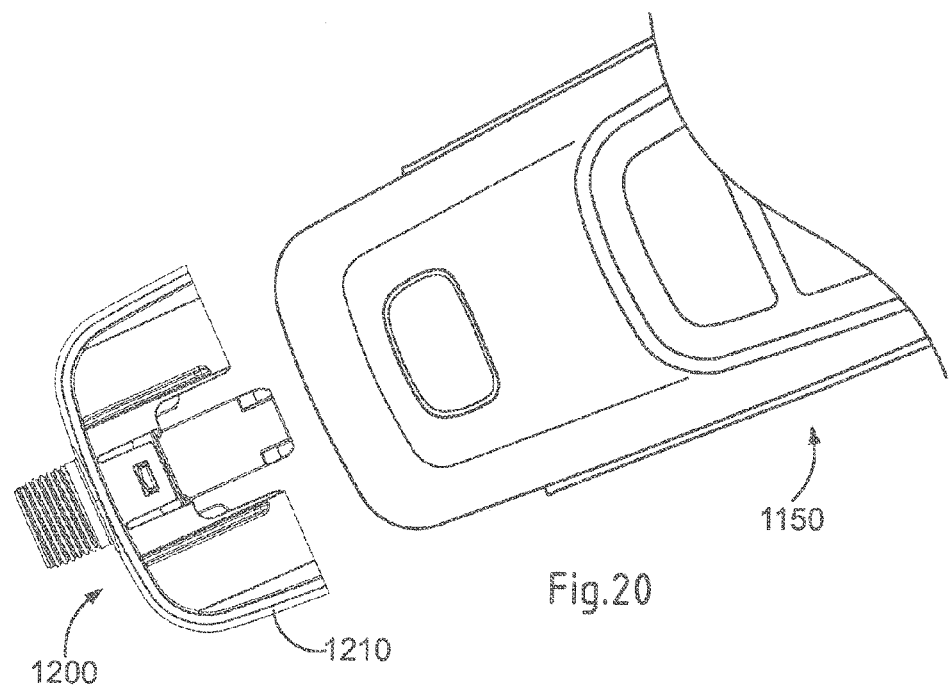
FIG. 20 illustrates a perspective view of the dispense interface illustrated in FIG. 15-16 about to be mounted onto the drug delivery device.

FIG. 20 illustrates the dispense interface 1200 illustrated in FIG. 12-13 about to be mounted onto a distal end of a drug delivery device. In this pre-attachment illustration, the lock out spring contained within the dispense interface 1200 resides in the first or initial position.

Figure 21:
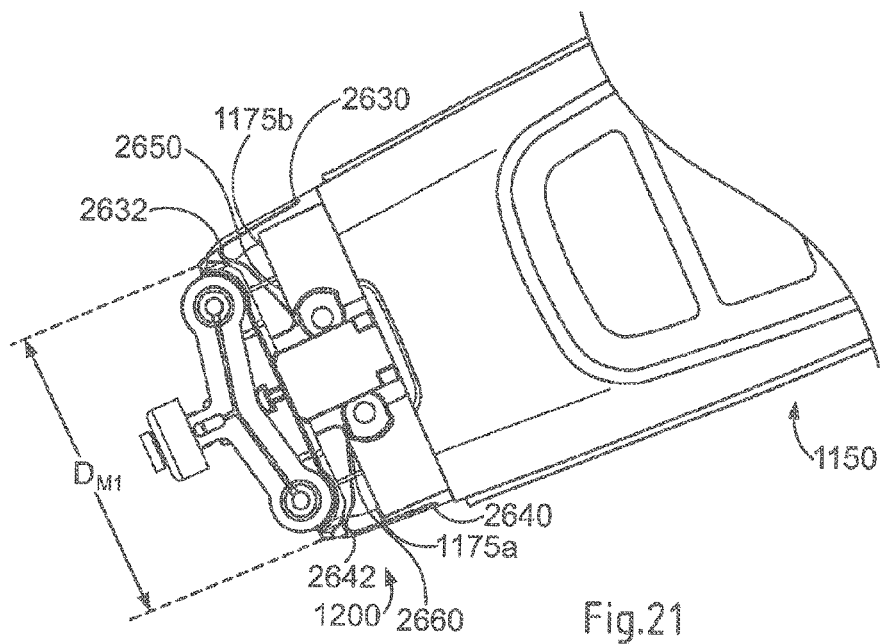
FIG. 21 illustrates a perspective view of the dispense interface in a partially seated position onto a drug delivery device.

FIG. 21 illustrates the dispense interface 1200 illustrated in FIG. 20 after the dispense interface has been moved to a first attached position. For ease of explanation, certain component parts of the dispense interface 1200 have been removed, such as the outer body 1210, so that the various configurations of the lock out spring may be illustrated and/or explained. For example, in this illustrated initial attached position, the outer body 1210 of the dispense interface 1200 has been removed so as to illustrate the lock out spring 2600 and how it changes state during attachment of the dispense interface to the drug delivery device. As illustrated, both the first and the second spring knuckles 2650, 2660 have entered the distal end of the drug delivery device and have made contact with a face of the cartridge holder. For example, the first spring knuckle 2650 has made contact with a first cartridge holder face 1175*b* and the second spring knuckle 2660 has made contact with a second cartridge holder face 1175*a*. As also illustrated, both the first and second lock out spring arms 2630, 2640 have entered the distal end of the drug delivery device and reside between the outer body of the device and the cartridge holders. However, as the dispense interface continues to move in the proximal direction from this initial illustrated position, the cartridge holder faces 1175*a*, 1175*b* begin to exert pressure on the first and second spring knuckles 2650, 2660. This exerted pressure tends to bend the first and second spring arms 2630. 2640 inwardly, towards one another so as to reduce the initial diameter DM1 of mouth.

Once the proximal end of the dispense interface 1200 enters the distal end of the drug delivery device 1150, when mounted onto the inner body 2000 of the dispense interface, the spring tip 2620 will be mounted on a retention rib provided on the inner body 2000. For example, FIG. 19 shows the lock out spring 2600 mounted on the inner body 2000 in a first or initial position. In this initial position, the spring tip 2620 resides over the retention rib 2090 on the inner body 2000. In addition, a bottom flat surface 2622 of the spring tip 2620 resides adjacent a flat distal surface of the first outer protrusion 2006 of the inner body 2000.

When in this initial condition, the arms of the spring are disposed to flex outwards, away from the center of the spring assembly. As such, as the dispense interface 1200 is fitted onto the distal end of the drug delivery device, the distal face of the device pushes on the lock out spring 2600, forcing the spring to move in the distal direction. This axial movement of the spring 2600 causes the spring to flex about its spring arms 2630, 2640. As these arms are restrained from rotating by the presence of the cartridge doors of the drug delivery device, the spring slides in the distal direction. This distal movement occurs until the spring tip 2622 snaps over the retention rib 2090 on the inner body 2000.

Figure 22:
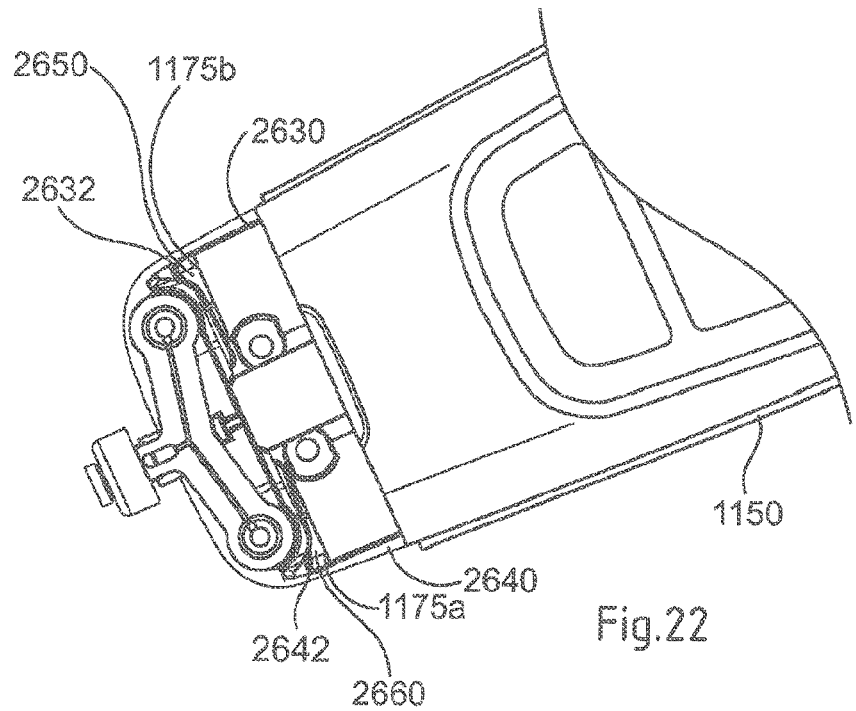
FIG. 22 illustrates a perspective view of the dispense interface illustrated in FIG. 21 in a fully seated position on a drug delivery device.

FIG. 22 illustrates the dispense interface 1200 illustrated in FIG. 21 in a fully seated position. As illustrated, in this fully seated position, both the first and second spring arms 2630, 2640 now reside along an outer surface of the cartridge holders and thereby exert an inwardly directed pressure against these cartridge holders. In addition, the first spring portion residing between first pivot point 2632 and the first knuckle 2650 flattens out along the first cartridge holder face 1175*b*. Similarly, the second spring portion residing between the second pivot point 2642 and the second knuckle 2660 also flattens out along the second cartridge holder face 1175*a*. Once the spring tip 2620 has snapped over the retention tip 2090 of the inner body 2000, the spring tip 2620 cannot be easily retracted in the proximal direction so as to allow the spring tip 2620 to move back over the retention rib 2090. As such, a spring force is built up in the first and second spring arms 2630, 2640 as they are forced against the cartridge housing until such a time as the dispense interface is removed from the device.

Figure 23:
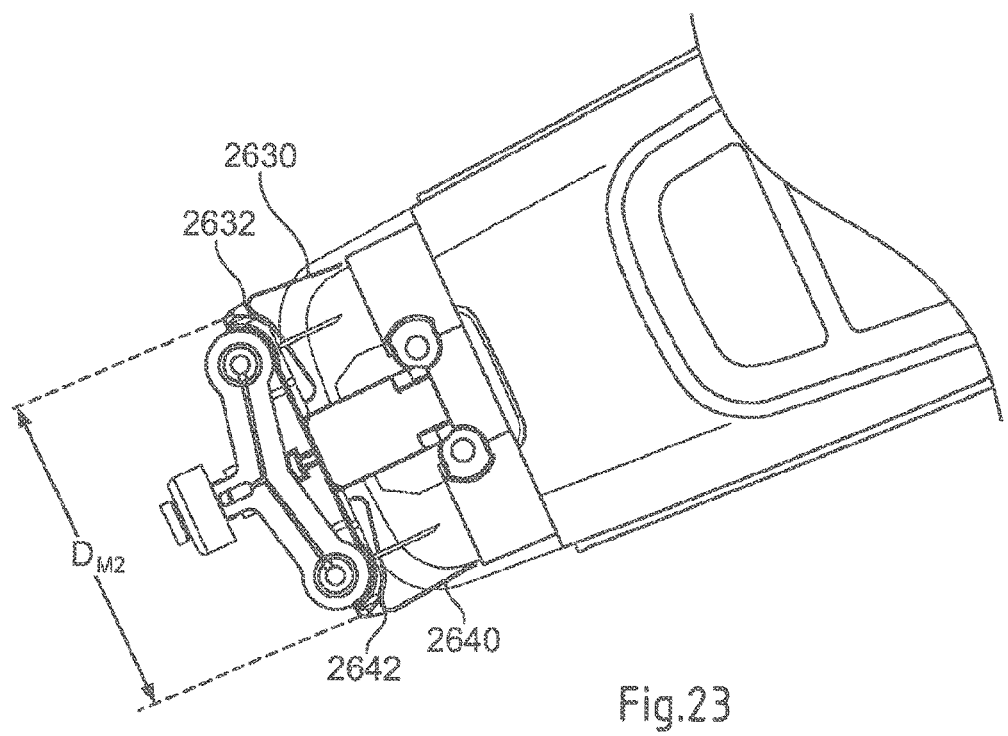
FIG. 23 illustrates a perspective view of the dispense interface illustrated in FIG. 22 in a partially removed position from a drug delivery device.

As discussed above, the release button on the drug delivery device may be pushed or manually activated so as to allow the user to remove the attached dispense interface 1200. FIG. 23 illustrates the dispense interface 1200 in a first position as it is being removed from the distal end of the drug delivery device 1150. As the dispense interface 1200 is removed from the device, the distal ends of the cartridge doors move out of engagement with the inwardly biased first and second spring arms 2630, 2640. As such, both spring arms 2630, 2640 are able to rotate as they relax and flex back towards one another.

Once the spring arms 2630, 2640 of the spring 2600 have rotated, they reside in an interference position which is illustrated in FIG. 23. For example, in this interference position, if one were to try to reattach the dispense interface 1200 onto the drug delivery device 1150, the spring arms 2630, 2640 would interfere with the distal end of the cartridge holders of the drug delivery device since these arms are no longer spaced apart the larger mouth distance DM1 as illustrated in FIG. 21 but are spaced apart a smaller mouth distance DM2. As such, the dispense interface 1200 is prevented from being reattached to the drug delivery device and thereby locks out or prevents the dispense interface 1200 from further attachment. The shape of the inner body 2000 and the support it gives to the spring help to ensure that the lock out spring 2600 cannot be easily forced or pushed out of the way by a user attempting to refit the dispense interface back onto the drug delivery device.

Figure 24:
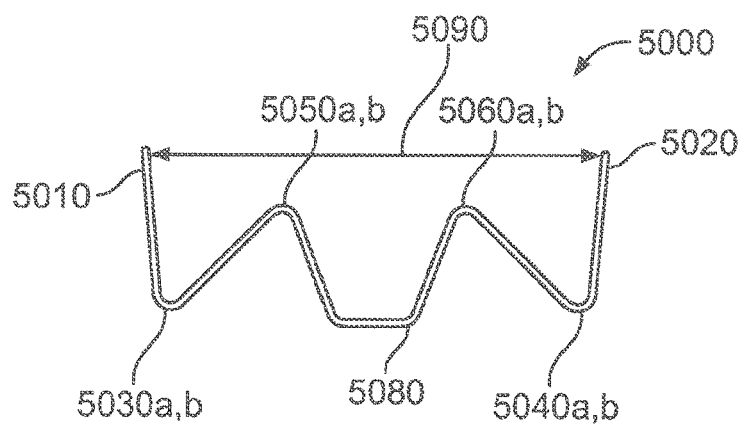
FIG. 24 illustrates a side view of an alternative arrangement of a locking member for use with a dispense interface.
Figure 25:
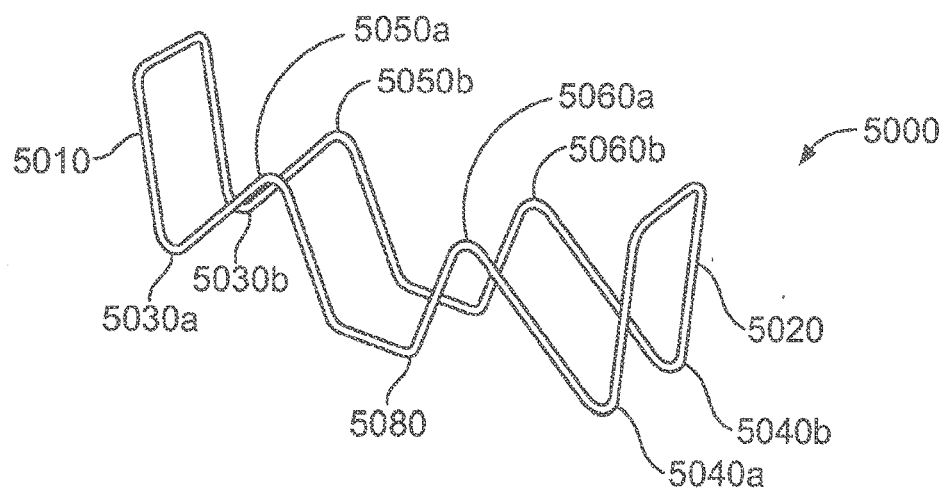
FIG. 25 illustrates a perspective view of the alternative locking member illustrated in FIG. 24.

The dispense interface may be used with a variety of different locking members or locking elements. For example, FIG. 24 illustrates a side view of an alternative arrangement of a locking element for use with a dispense interface and FIG. 25 illustrates a perspective view of the alternative locking element illustrated in FIG. 24. FIG. 24 illustrates a side view of an alternative locking element 5000 in the form of a wireform locking member. As illustrated in FIGS. 24 and 25, this locking member 5000 comprises a first and a second wing 5010, 5020, a first and a second pivot point 5030, 5040, first and second knuckles 5050, 5060 and a clip region 5080. A mouth 5090 of the spring 5000 may be described as the width or distance between the first and the second wings 5010, 5020.

Figure 26:
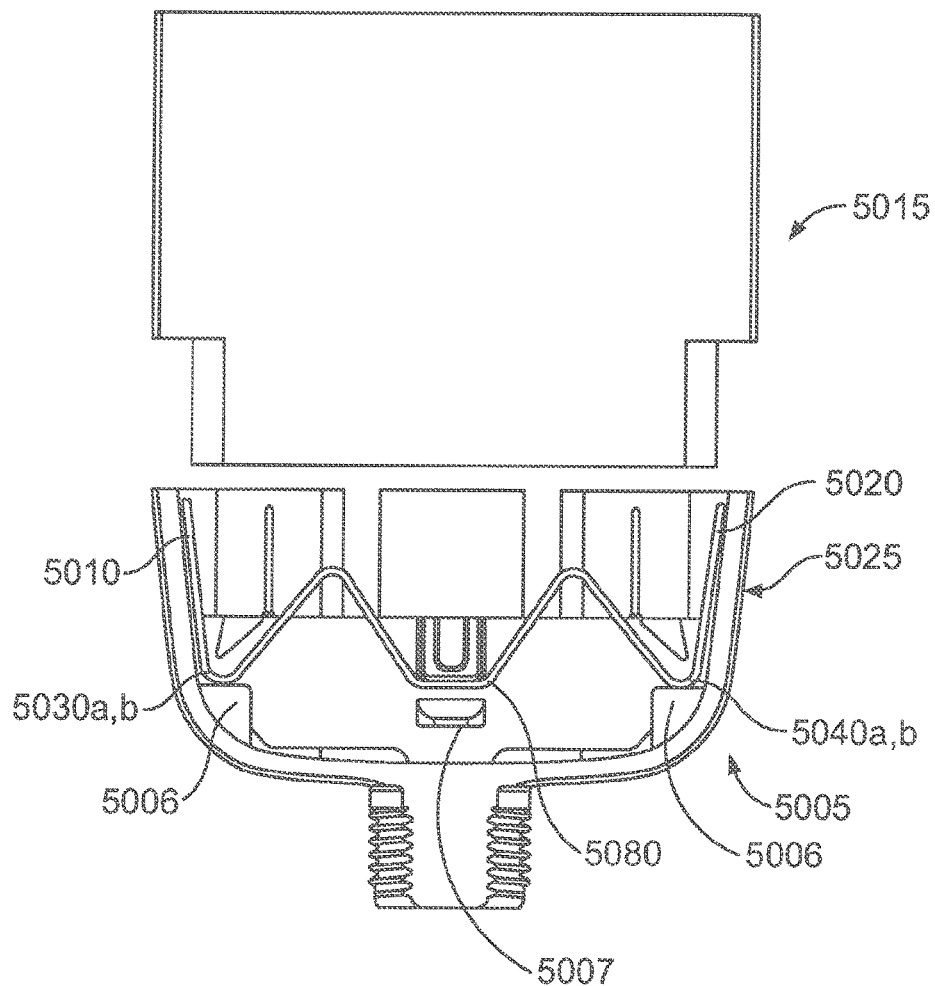
FIG. 26 illustrates a cross-sectional view of the alternative locking member illustrated in FIGS. 24-25 with the dispense interface about to be mounted onto a distal end of a drug delivery device.

FIG. 26 illustrates a cross-sectional view of the alternative locking member illustrated in FIGS. 24-25 within a dispense interface and about to be mounted onto a distal end of a drug delivery device. As illustrated, the wireform lockout element 5000 is positioned within a dispense interface where the dispense interface 5005 is provided in a receptive condition: that is, in an unused condition (i.e. not locked out) and as received by a user. As illustrated, the first and second wings 5010, 5020 of the wireform lockout element 5000 abut an inner face of an outer hub 5025 of the dispense interface 5005. The pivot points 5030*a*, 5030*b*, and 5040*a*, 5040*b* reside along a distal shelf 5006 provided internally on the dispense interface outer body. The clip region 5080 of the wireform lockout element 5000 is also illustrated as residing on the proximal side of a non-return clip 5007 of the inner body of the dispense interface 1200.

In this pre-installed first position, the wireform lockout element 5000 may be captured between the inner and outer hub chassis components of the dispense interface 5005. As illustrated, a proportion of the lockout element 5000 resides below a top surface of the inner body of the dispense interface 5005. Preferably, this area is largely inaccessible to the user. The first and second wings 5010, 5020 protrude significantly above this surface and lie close to the side wall of the outer chassis at either end of the dispense interface. The knuckles 5050, 5060 of the lockout element 5000 also protrude above this surface into the accessible region of the dispense interface 5005.

In the receptive condition as illustrated in FIG. 26, the wing portions 5010, 5020 of the wireform lockout element 5000 are open. That is, the wing portions 5010, 5020 of the wireform lockout element 5000 make a positive angle about the vertical axis. The "mouth" 5090 of the lockout element 5000 may be defined as being in an open state. In this condition, the distance across the wing tips 5010, 5020 is greater than the width of the portion of the drug delivery device 5015 onto with the interface 1200 attaches. In this way, the wing portions of the wireform lockout element 5000 pass around the distal end of the drug delivery device 5015, thereby allowing the dispense interface 1200 to be fitted onto the device.

FIG. 27 illustrates a cross-sectional view of the alternative locking member illustrated in FIGS. 24-25 in the dispense interface 5005 and mounted onto a distal end of a drug delivery device 5015. As illustrated, during fitment of the dispense interface 5005 onto the drug delivery device 5015, the wireform lockout element begins to knuckle. In pushing the dispense interface to the fully on or home position, the knuckles 5050, 5060 and clip regions or portions 5060, 5080 of the wireform lockout element are forced in a forward or distal direction, away from the drug delivery device 5015. The clip portions 5060, 5080 ride over a pair of non-return clips on (either side of the) the dispense interface 5005. In FIGS. 26-27, only one non-return clip 5007 is illustrated. The non-return clips 5007 engage the wireform lockout element and hold it in the forward (or activated) position as illustrated in FIG. 28.

The advanced positions of the knuckle and clip regions of the lockout element 5000 create a moment about the pivot points 5030, 5040. This moment acts to bias the wings 5010, 5020 in an inwards direction towards one another. However, with the dispense interface still attached, the distal end of the drug delivery device substantially fills the lockout element mouth 5090, hence the wings 5010, 5020 are restricted and are able to close in by only a small amount. Strains are induced in the lockout element 5000 particularly in the region of the pivot points 5030, 5040 and the wings 5010, 5020 come to rest on the drug delivery device 5015, pinching it at the sides. The clamping effect provided by the wings is relatively small, and results in a marginal increase in force required to remove the hub.

FIG. 28 illustrates a cross-sectional view of the alternative locking member 5000 illustrated in FIGS. 24-25 in a locked condition after the dispense interface 5005 has been removed from the distal end of a drug delivery device. When the dispense interface 5005 is removed from the device 5015, the tips of the wings 5010, 5020 will slide or drag across the side surface of the drug delivery device. When the dispense interface 5005 is removed such that the device is clear of the interlock member mouth, the wings 5010, 5020 will close further in the inwards direction, rotating about the pivot point. The interlock member mouth closes in and the interlock comes to rest in the locked condition. The wings come to rest at a position where they make a negative angle with the vertical.

With the lockout element 5000 in the locked out condition as illustrated, the spring mouth is now narrower than the width of the distal end of the drug delivery device 5015 around which the cartridge hub fits. As such, the dispense interface 5005 is prevented from being reattached to the distal end of the drug delivery device 5015.

Attempting to re-attach the dispense interface 5005 back onto the distal end of the drug delivery device 5015 will result in vertical loading on the wing tips. A vertical load will attempt to further close the mouth 5090 as the wing tips are now inboard of the pivot points of the wireform lockout element 5000. However, the outer retaining bosses limit the extent to which the wings can be forced in this inwards direction. Since the wings 5010, 5020 remain within a few degrees of the vertical, applied vertical loads will largely be translated down the wings, through the pivot points and into the outer chassis.

Excessive load conditions may cause the locking member wings 5010, 5020 to buckle. Under such conditions, the wings will deflect inwards and will contact and may cause damage to the dispense interface such as bending the needles contained within the hub. Regardless of the lockout this will render the needle element of the dispense interface 5005 not capable of being remounted onto the drug delivery device 5015 and therefore not capable of being used for a second dose administration.

Furthermore, a user may attempt to open the spring mount by manipulating the wings in an attempt to reset the locking element 5000 to the original receptive condition as illustrated in FIG. 26. However, this effect will be, at best, temporary. That is, in one arrangement, the wings cannot be deflected far enough to cause permanent deformation. Upon release, the wings will return to the locked condition as illustrated in FIG. 28. A true reset might be achieved by overcoming the non-return clips 5007. For this reason, this particular area of the dispense interface 5005 may be inaccessible to the user.

Different lockout element arrangements have been described in the context of certain embodiments such as those illustrated in FIGS. 18 and 24. However, it should be recognised that there are a number of further alternative arrangements of a lockout element. A few exemplary alternative lockout element arrangements are generally described below.

As illustrated in FIGS. 24-28, in one arrangement, the lockout element may comprise a wireform lockout element. However, the lockout element might equally be produced from a formed spring sheet or a similar suitable form. The lockout element could, for example, be produced from a flexible moulded plastic part.

Alternatively, the lockout element may be constructed so as to comprise a plurality of lockout element portions. As one example, the lockout element may comprise two or more separate sprung forms.

Alternatively, the lockout element may be partially replaced by rigid parts. As one example, the lockout element wings 5010, 5020 of the wireform member 5000 illustrated in FIGS. 24-28 could be constructed as solid parts with a separate or integrated spring element.

In addition, the lockout element may include a clip that is positioned at alternative locations and take various different forms. As one example, the lockout element may comprise a clip.

The clip may be replaced by an alternative means of retaining the lockout element in the locked/clipped condition. As one example, the spring may feature a continuous non-return slide way as provided by rearward biased teeth.

In one alternative arrangement, the lockout element may have no clip at all. Rather, the lockout element may instead be maintained in the receptive and locked condition due to an over-centering action. Alternatively, the lockout element may be permanently biased upwards (i.e., in the proximal direction) in the locked position and have a mechanism or means of holding it in the splayed/receptive condition.

The lockout element knuckles may be configured in a different form and may for example form a platform that partially or substantially covers the top surface.

For example, FIG. 29 illustrates a perspective view of an alternative arrangement of a locking member for use with a dispense interface. As illustrated, FIG. 29 illustrates a perspective view of an alternative arrangement of a lockout component 5200. FIG. 30 illustrates a cross-sectional view of the locking member illustrated in FIG. 29 within a dispense interface with the locking member in a receptive condition.

In this arrangement, the lockout component 5200 comprises a plurality of knuckles 5050*a*, 5050*b* and 5260*a*, 5260*b* that are formed by an enlarged platform region located near a central location of the lockout component 5200. The platform region is located between a first wing 5210 and a second wing 5220. A clip of the lockout element 5200 is created by a ramped and then flat region on the inner hub chassis that engages with the lockout component in two positions, and on either side of the dispense interface 5025. FIG. 30 illustrates this alternative lockout element 5200 within a dispense interface 5025 where the dispense interface is provided in a receptive condition.

To lock out the lockout element 5200, the dispense interface 5025 is mounted onto the drug delivery device utilizing retention region 5026 and this will lock the member. FIG. 31 illustrates this lockout element 5200 in a lockout condition.

FIG. 32 illustrates a perspective view of another arrangement for a lockout element 5400. In this arrangement, the lockout element comprises a clip spring where knuckles of the lockout element 5400 are formed by an enlarged platform region 5480. For example, FIG. 33 illustrates this alternative lockout element arrangement in the form of a clip spring where the clip spring resides in a receptive condition. For ease of illustration, only certain elements of the dispense interface are illustrated. Here, the lockout element 5400 is positioned on the inner body of the dispense interface 5405. As illustrated, the dispense interface comprises a first and a second tab 5030, 5040 and resides in a receptive condition. The clip or retaining feature is created on the inner hub chassis that engages with the tabs 5030, 5040 at either end of the spring, in the gap created between the legs of the wings 5010, 5020. FIG. 34 illustrates the lockout spring arrangement 5040 in a locked condition. As illustrated, the tabs 5030, 5040 have moved in a distal direction while the enlarged platform region 5480 has also moved in a distal direction and now resides along the flat surface of the inner body of the dispense interface. The tabs 5030, 5040 are retained in this distal position by a second set of distal retention features formed by the inner body of the dispense interface. With the lockout element 5400 in the locked out condition, the mouth 5490 of the locking member 5400 is now narrower than the width of the distal end of the drug delivery device. As such, the dispense interface 5405 is prevented from being reattached to the distal end of the drug delivery device. Attempting to re-attach the dispense interface 5405 back onto the distal end of the drug delivery device will result in vertical loading on the wing tips 5010, 5020. A vertical load will attempt to further close the mouth 5490 as the wing tips 5010, 5020 are now inboard of the pivot points of the lockout element.

FIG. 35 illustrates a perspective view of yet another arrangement of a lockout element 5600 comprising a plurality of lockout element portions. Here, the lockout element portions comprise similar first and a second spring forms 5602, 5604. In this illustrated arrangement, the first spring form 5602 is provided with a wing 5610 and the second spring form 5604 is similarly constructed and comprises a wing 5620 as well. FIG. 36 illustrates the lockout spring arrangement 5600 where the dispense interface 5605 resides in a receptive condition. As illustrated in this receptive condition, a clip is created by a return on the spring ends of the lockout spring arrangement 5600. In this arrangement, the first spring portion 5602 comprises spring ends 5630a, 5630b and the second spring portion 5604 comprises spring ends 5640a, 5640b. These spring ends 5630a, 5630b and 5640a, 5640b pass through a gap created between a boss feature 5650 on the inner hub chassis and a ribs 5560, 5670 on the outer hub chassis FIG. 37 illustrates the twin spring lockout arrangement 5600 in a locked condition. In this locked condition, the spring ends 5630a, 5630b and 5640a, 5640b of the lockout spring member 5600 are removed from the gap created by the boss feature and now reside (locked) on the distal side of the non-return clip.

FIG. 38 illustrates a perspective view of yet another arrangement of a lockout element 6200 for use with a dispense interface 6205. FIG. 39 illustrates a cross section view of the lockout element 6200 within a dispense interface 6205 in a receptive condition.

The lockout element 6200 comprises a first and a second wing members 6210, 6220 that extend from a first shoulder 6240 and a second shoulder 6250, respectively. In this arrangement, the lockout element 6200 is assembled and then provided in a receptive condition where the lockout element 6200 is provided in a stored energy state where the two wings 6210, 6220 are biased inwards or towards one another. The wings 6210, 6220 are held open (in a receptive condition) and held in such a biased state by stepped features 6230, 6235 provided near the outer ends of the inner body (stepped features may be seen from FIG. 41). These stepped features 6230, 6235 are provided along an outer surface of the inner body of the dispense interface 6205 and act as a retaining feature, retaining the lockout element in the biased state. As such, when the dispense interface and hence the inner body is fitted to the distal end of the drug delivery device, the drug delivery device pushes against the shoulder portions 6240, 6250 of the locking element 6200. FIG. 40 illustrates the dispense interface 6205 with the locking element 6200 in an activated state. Action of the drug delivery device against these shoulder portions 6240, 6250 forces the locking member 6200 to advance. In doing so, the locking member 6200 is pushed off the stepped retaining features 6230, 6235 which previously held the locking member 6200 in an open position. The locking member 6200 closes in against the device sidewall, upon removal the locking member wings close further to the locked condition.

In the described embodiment, the locking member 6200 is activated by a downwards movement that releases the locking member 6200 from a feature which keeps the spring mouth open. Alternative ways of holding the locking member 6200 open and for providing actuation may also be used. As just one example, one alternative arrangement would include the provision of deformable retaining features on either the inner body of the dispense interface 6205 or the locking member that are acted upon by the distal end of the drug delivery device.

Figure 43:
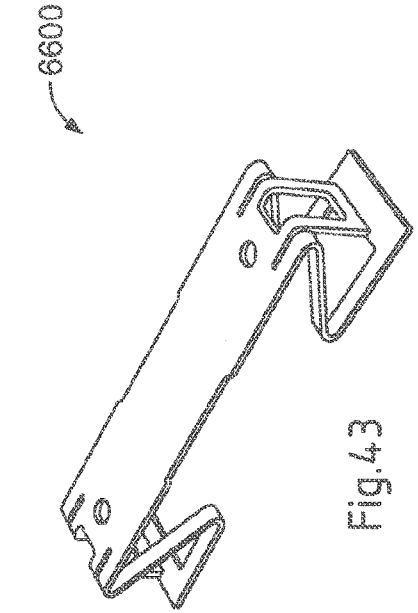
FIG. 43 illustrates a perspective view of an alternative arrangement of a locking member for use with a dispense interface.
Figure 42:
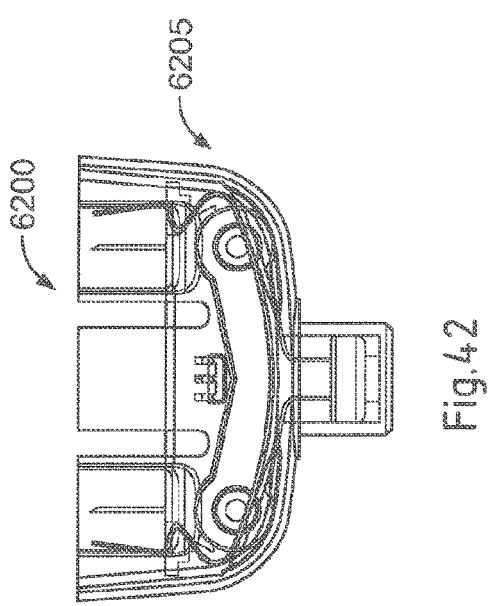
FIG. 42 illustrates a cross-sectional view of the locking member illustrated in FIG. 38 within a dispense interface with the locking member in a locked condition.
Figure 45:
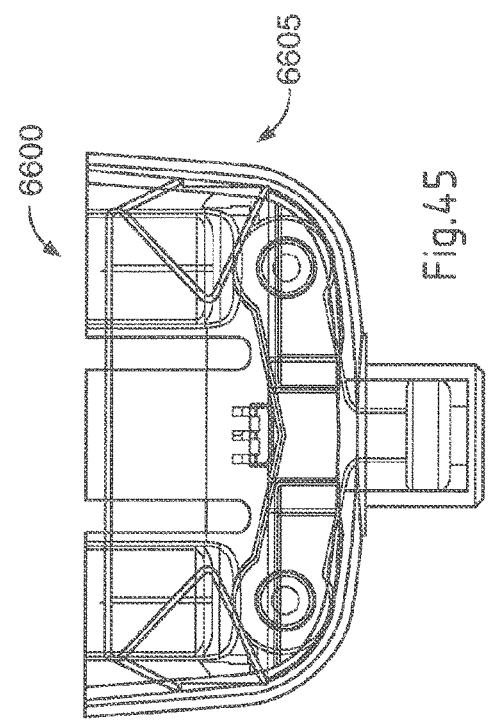
FIG. 45 illustrates a cross-sectional view of the locking member illustrated in FIG. 43 within a dispense interface with the locking member in an locked condition.
Figure 44:
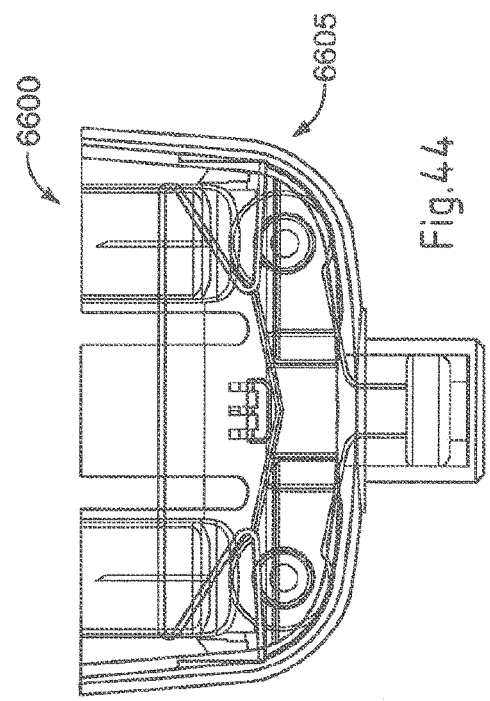
FIG. 44 illustrates a cross-sectional view of the locking member illustrated in FIG. 43 within a dispense interface with the locking member in a receptive condition.

FIG. 43 illustrates yet another alternative locking member arrangement for use with a dispense interface. Specifically, FIG. 43 illustrates a perspective view of a locking element 6600 comprising a platform spring. This platform locking member embodiment comprises a rising lockable platform that provides a lockout functionality. FIG. 44 illustrates a dispense interface 6605 comprising a platform spring locking element 6600 in the receptive condition. In this illustrated arrangement, the platform locking element 6600 is held in a strained state on assembly. Upon fitting to the distal end of the drug delivery device, the springs are release from various clip or retaining features, and remain held down only by the drug delivery device. When the device is removed, the springs extends to form a general platform across the internal area of the inner body of the dispense interface. For example, FIG. 45 illustrates the platform spring 6000 in a locked condition. In one arrangement, the platform has one or more one way features, for example sprung teeth which are angled teeth (which further engage features on the inner/outer chassis) which provide the lockout, thus preventing the platform locking element from returning to a receptive state.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface for use with a drug delivery device, the dispense interface comprising:
   a distal end; and,
   a proximal end configured to be seated about a distal end of the said drug delivery device;
   an outer body and an inner body contained within the outer body, where the outer body has a mounting hub provided at the distal end of the dispense interface and the inner body is coupled to an inner surface of the outer body,
   a lockout element being arranged within the outer body of the dispense interface, wherein the lockout element comprises a first wing portion and a second wing portion,
   wherein the lockout element is maintained in a first position,
   wherein the lockout element in the first position is configured to move into a second position when the dispense interface is first attached and then removed from said drug delivery device, wherein the first wing portion and the second wing portion are closer to each other in the second position than in the first position so as to prevent said dispense interface from being reattached to the drug delivery device in the second position,
   wherein the lockout element is arranged in the first position such that it is engaged by the drug delivery device on attachment of the dispense interface to the drug delivery device and moved into a third position,
   wherein the lockout element is configured to move from the third position to the second position on removal of the drug delivery device from the dispense interface.

2. The apparatus according to claim 1, wherein the lockout element comprises a spring assembly.

3. The apparatus according to claim 2, wherein the spring assembly comprises two or more sprung forms.

4. The apparatus according to claim 2, wherein the spring assembly comprises at least one of the first and second wing portions comprising a rigid component.

5. The apparatus according to claim 1,
   wherein the lockout element comprises at least one knuckle portion configured to be contacted by the drug delivery device on attachment of the dispense interface to the drug delivery device, wherein the lockout element comprises a pivot point for each of the first and second wing portions, and, wherein each of the first and second wing portions is configured to bend inward around the respective pivot point when the lockout element moves to the second position.

6. The apparatus according to claim 1, wherein the dispense interface comprises a retention arrangement configured to maintain the lockout element in the first position until the lockout element is engaged by the drug delivery device on attachment of the dispense interface to the drug delivery device.

7. The apparatus according to claim 6, wherein the retention arrangement comprises at least one stepped feature on the inner body of the dispense interface and wherein the lockout element in the first position is configured to be pushed off the at least one stepped feature upon engagement by the drug delivery device on attachment of the dispense interface to the drug delivery device.

8. The apparatus according to claim 1, wherein the dispense interface comprises a retention arrangement, configured to maintain the lockout element in the second position and wherein the lockout element is arranged in the first position such that it is engaged by the drug delivery device on attachment of the dispense interface to the drug delivery device and moved into the second position.

9. The apparatus according to claim 8, wherein the retention arrangement comprises at least one non-return clip configured to maintain the lockout element in the second position and wherein a clip portion of the lockout element is configured to ride over the at least one non-return clip when it is moved into the third position.

10. The apparatus according to claim 8, wherein the retention arrangement comprises at least one retention region which is ramped and then steps back to a flat region in a distal direction of the dispense interface, which at least one retention region is arranged on the inner body of the dispense interface and which at least one retention region is configured to engage the lockout element symmetrically on at least two surfaces of contact in the second position.

11. The apparatus according to claim 8, further comprising a tab at each end of the lockout element facing in a distal direction, wherein each respective tab is arranged between the corresponding first or second wing portion and wherein the lockout element comprises a platform region configured to be engaged by the drug delivery device on attachment of the dispense interface to the drug delivery device.

12. The apparatus according to claim 8, wherein the lockout element comprises two symmetrical spring forms, wherein each spring form comprises a hooked end, wherein the retention arrangement comprises at least one boss feature on the inner body of the dispense interface and further comprises at least one rib on the outer body of the dispense interface, wherein one of the at least one boss feature and one of the at least one rib are arranged to provide a gap in between and wherein each hooked end is configured to move through the gap between a boss feature and a corresponding rib when the lockout element is engaged by the drug delivery device on attachment of the dispense interface to the drug delivery device.

13. A dispense interface for use with a drug delivery device, the dispense interface comprising:

a distal end; and, a proximal end configured to be seated about a distal end of the said drug delivery device;

an outer body and an inner body contained within the outer body, where the outer body has a mounting hub provided at the distal end of the dispense interface, the mounting hub configured to be releasably connected to a needle assembly and the inner body is coupled to an inner surface of the outer body, a lockout element being arranged within the outer body of the dispense interface, wherein the lockout element comprises a first wing portion and a second wing portion, wherein the lockout element is maintained in a first position, wherein the lockout element in the first position is configured to move into a second position when the dispense interface is first attached and then removed from said drug delivery device, wherein the first wing portion and the second wing portion are closer to each other in the second position than in the first position so as to prevent said dispense interface from being reattached to the drug delivery device in the second position, wherein the lockout element is arranged in the first position such that it is engaged by the drug delivery device on attachment of the dispense interface to the drug delivery device and moved into a third position, and wherein the lockout element is configured to move from the third position to the second position on removal of the drug delivery device from the dispense interface.

* * * * *